United States Patent
Berlad et al.

(10) Patent No.: US 6,242,745 B1
(45) Date of Patent: Jun. 5, 2001

(54) SOLID STATE GAMMA CAMERA

(75) Inventors: Gideon Berlad, Haifa; Yaron Hefetz, Herzelia, both of (IL)

(73) Assignee: GE Medical Systems Israel Ltd., Tirat-Hagarmel (IL)

( * ) Notice: Subject to any disclaimer, the term of this patent is extended or adjusted under 35 U.S.C. 154(b) by 0 days.

(21) Appl. No.: 09/308,808

(22) PCT Filed: Nov. 24, 1996

(86) PCT No.: PCT/IL96/00164

§ 371 Date: May 24, 1999

§ 102(e) Date: May 24, 1999

(87) PCT Pub. No.: WO98/23974

PCT Pub. Date: Jun. 4, 1998

(51) Int. Cl.⁷ .................................................... G01T 1/24
(52) U.S. Cl. ........................ 250/370.1; 250/370.06; 250/370.09; 250/370.01
(58) Field of Search ........................... 250/366, 367, 250/369, 361 R, 363.02, 370.01, 370.06, 370.1, 370.11, 370.12, 370.13, 370.14, 371

(56) References Cited

U.S. PATENT DOCUMENTS

| | | |
|---|---|---|
| 4,432,059 | 2/1984 | Inbar et al. . |
| 4,672,207 | 6/1987 | Derenzo . |
| 5,117,114 * | 5/1992 | Street et al. ................... 250/370.11 |
| 5,548,122 | 8/1996 | Shoji . |
| 5,723,866 * | 3/1998 | Hamilton, Jr. .................. 250/370.09 |
| 5,825,033 * | 10/1998 | Barret et al. ...................... 250/370.1 |
| 5,847,396 * | 12/1998 | Lingren et al. ...................... 250/369 |

FOREIGN PATENT DOCUMENTS

| | | |
|---|---|---|
| 2262383 | 6/1993 | (GB) . |
| 2274964 | 8/1994 | (GB) . |
| 2 289 979 | 12/1995 | (GB) . |
| WO 95/33332 | 12/1995 | (WO) . |

* cited by examiner

Primary Examiner—Constantine Hannaher
Assistant Examiner—Albert Gagliardi
(74) Attorney, Agent, or Firm—Fenster & Co. Patent Attorneys, Ltd.

(57) ABSTRACT

A gamma camera head including:

a plurality of signal sources, each associated with a pixel position, the source producing a signal when a gamma ray absorption event occurs at or sufficiently close to its associated pixel, wherein the plurality of signal sources is associated with a contiguous extent of pixels; and a plurality of electronic circuits, each of which receives signals from at least two of the plurality of signal sources, wherein each circuit receives the signals only from sources associated with non-contiguous pixels.

37 Claims, 16 Drawing Sheets

SOLID STATE GAMMA CAMERA

RELATED APPLICATIONS

This application is a national phase application of PCT application PCT/IL96/00164, filed Nov. 24, 1996.

FIELD OF THE INVENTION

The present invention relates to methods for reading out a matrix of elements in a Solid State Gamma Camera.

BACKGROUND OF THE INVENTION

The use of solid state detectors for the detection of ionizing radiation is well known. Furthermore, the use of a mosaic of groups of detector electrodes on a single substrate of material such as CdZnTe has been mooted.

However, the application of such a matrix in a practical gamma camera is nearly obviated by the lack of a suitable fast readout system capable of reading out individual counts from the very large array of detector electrodes desirable for such a camera.

U.S. Pat. No. 4,672,207 describes a readout system for a mosaic of NXM scintillator/photodetector elements. In this system the photodetectors feed row and column amplifiers which indicate, for signals having the proper pulse height, that an event has occurred in the nth row and the mth column of the mosaic. However, this system requires a large number of scintillator crystals and, if applied to the solid state CdZnTe camera, as postulated above, would be unable to discriminate events which occur near or at the boundary between elements or to discriminate events which result in Compton scattering events.

In published PCT Application WO 95/33332 a method of reading out a matrix is described in which charge, generated as a result of events at points in the matrix, is stored at those points and the entire matrix is read out seriatim. This method, although mooted as being useful for a gamma camera utilizing CdZnTe, CdTe or a number of other materials at pages 45–48, is not capable of distinguishing individual events which would be necessary for the energy discrimination of events, used, for example, to eliminate events caused by Compton scattering.

SUMMARY OF THE INVENTION

It is an object of the present invention to provide a solid state gamma camera system having an improved readout system.

It is an object of some aspects of the present invention to provide a solid gamma camera system in which the outputs of individual pixels are recorded without the need to individually address the pixels.

It is an object of some aspects of the present invention to provide a solid state gamma camera in which events which occur near the boundaries of pixels and to some extent near the boundaries of crystals are properly detected.

It is an object of some aspects of the present invention to provide a solid state gamma camera in which the cells are all in a "talk-only" mode, in which no noise producing interrogating signals are necessary and in which each pixel transmits its data immediately after it detects an event.

It is an object of some aspects of the invention to provide a system which detects events which produce signals in more than one pixel, without collision of the data which is generated on these adjoining pixels.

A solid state gamma camera, in accordance with a preferred embodiment of the invention, is made up of a mosaic of crystals of CdTe (or alternatively of CdZeTe, $HgI_2$, InSb, Ge, GaAs, Si, PbCs, PbS or GaAlAs). One side of each crystal is preferably covered by a single, common, electrode and the other side of the crystal is preferably covered by a rectangular (preferably square) matrix of closely spaced electrodes. This matrix of electrodes defines the cells or pixels of the gamma camera image. In a preferred embodiment of the invention, the matrix comprises 16×16 elements having a size of 2×2 mm. However, the size of the elements and the matrix size may vary over a relatively wide range depending on the desired spatial resolution and count rate. In particular, crystal sizes of 1×1 to 4×4 mm appear to be reasonable in the practice of the invention.

Generally, a rectangular mosaic of crystals each with its associated matrix of elements is used to provide a camera of the required size. This mosaic may have a dimension of 20×20 crystals or greater.

When a gamma ray impinges on the crystal, energy which is transferred to the crystal creates charge carriers within the normally insulating crystal such that it becomes temporarily conducting. When a high voltage is applied between the electrodes in the matrix and the common electrode, this charge generation results in current flow between them. This current generally lasts between 50 and 600 nanoseconds, depending on the depth of penetration of the gamma ray prior to its interaction with the crystal, and the crystal quality. The total charge collected by the matrix of elements is substantially proportional to the energy of the absorbed gamma ray. In this regard, each element can be considered as a signal source which produces a signal when a gamma ray absorption event occurs at or sufficiently close to its associated pixel.

In principle, the current resulting from a particular event (i.e., an absorbed gamma ray) should be limited to a single element of the matrix. However, a number mechanisms act to cause current to be measured at, generally, adjoining matrix elements.

One type of mechanism which induces current in more than one electrode is when an event occurs at or near a boundary between two or four matrix elements. Clearly, an event which occurs precisely at the boundary will cause an equal division of current between the adjacent two or four electrodes. Furthermore, events which occur near a boundary will also cause current to flow in adjoining elements since the gamma ray creates a small, but finite cloud of charge carriers which may overlap more than one cell and which diffuses and widens during its travel toward the electrodes. Thus, part of the current associated with an event near the boundary will be detected in an adjacent pixel element.

For each of the above effects, the energy of the gamma ray is deposited at substantially one point in the crystal and its effects are measured at more than one pixel element. Some events do not deposit their energy at only one point in the crystal. Rather they may undergo Compton scattering so that a portion of their energy is deposited at various points in the crystal. Each of these energy deposits causes currents to flow in corresponding pixel elements.

The above effects are dependent on both the energy of the gamma ray photons and the depth of penetration of the photon when it interacts with the crystal. Higher energy photons produce a larger electron cloud and have a higher probability of Compton scattering, such that, for 500 KeV photons, less than half will deposit their energy at a single point. The depth of penetration of the photon will determine the amount of spreading of the electron cloud prior to its being collected by one or more of the matrix elements.

While there is a relatively large probability that current will be collected in neighboring electrodes, the probability that current will be collected by non23 neigbboring electrodes is small, for the energies used in Nuclear Medicine.

The determination of the position and energy of an event, especially for the situation where more than one matrix element receives current from the event, requires that (i) current generated by each event be separately received for each event and (ii) that the response at each matrix element be separately received, or at least that all currents for a particular event be added to give a proper measure of the energy of the event. This would appear to require that each pixel be connected, separately or in a multiplex fashion, to the main data processing computer. Such a connection would be impractical.

In accordance with a preferred embodiment of the present invention a pre-processing and multiplexing unit is attached to each crystal. This unit, referred to herein as an "ASIC" unit, determines the distribution of charge (i.e., energy) associated with each event and the position of the event. For events whose charge is associated with more than one pixel, the ASIC unit determines the amount of charge associated with each of the pixels. It is this reduced amount of information, namely, the energy associated with each pixel which is involved in an event and the position of each of these pixels which is collected.

In accordance with a preferred embodiment of the invention, the pixels on each crystal are grouped in K identical rectangular groups of nxm pixels, designated $P_i$, (i=1,2, ... K) in a raster manner. The positions of the pixels in each group are designated as $P^j$ (j=1,2, L=nxm) in a raster manner. Thus, $P_i^j$ completely define the pixel in the crystal. The preconditioned voltages from electrodes having the same value of i are connected to the inputs of the same ASIC. Under normal circumstances, in which each element is separately interrogated, Kxnxm lines would be needed.

The basis for a reduction in the number of lines required to specify the position and strength of an event in the crystal is based on the fact that most events produce charge and current in one pixel and at most in 2–4 contiguous pixels. Thus if nxm is at least 2x2, signals can only be generated in no more than one pixel for each of the K groups. The pixels may be in adjacent groups, however, the i designation of the pixel in the adjacent groups will be different for any event.

Each ASIC produces a coded output of the position of the group from which the signal was received, a voltage proportional to the charge generated at the electrode and, preferably, an output which indicates that an event has occurred.

For example, consider a crystal having a matrix of 16x16 pixels grouped into 64 (8x8) groups of 2x2 pixels. Such a crystal has four ASICs, one for each position in the group. Each ASIC (having 64 input lines, one for each group) thus requires 8 output lines to completely describe the portion of the charge generated at the electrodes. One of the lines carries the signal amplitude (analog) and six lines are required for the address. In addition a eighth line preferably carries the "event occurred" signal.

Associated with each crystal is a module carrier which carries the ASICs associated with the crystal, e.g., four ASICs for the preferred embodiment. The total number of lines need to specify the position and intensity of an event in a crystal is thus, for the preferred embodiment, 8x4=32 lines. While the number of "event occurred" lines could be reduced by combining the signals from the various ASICs, it is preferable to utilize a separate "event occurred" line for each ASIC to avoid residual signals on the other lines being considered by the computer.

It is understood that the time required to detect an event internally inside the ASIC depends on the time required to collect all the charge (a few hundred nanoseconds to 1 microsecond or more depending on the circuitry used). However, the time the lines are busy may be much shorter, since this time can be as short as the time it takes to stabilize the analog signal on the output lines plus the time it takes for the A/D conversion at the computer end. Using presently available components a "line busy" time of 100 nanoseconds or even 50 nanoseconds is easily attainable. This "line busy" time is the factor which limits the rate of event collection. At the end of this time the ASIC is preferably reset.

Generally, a gamma camera will comprise a number of crystals in a mosaic. If the speed required of the camera is slow, i.e., it is sufficient to detect one event per event time cycle, a further reduction in the number of lines from the camera into the computer can be achieved. In this case the energy outputs from all the ASICs are summed and the addresses are combined to give the address of the events in a larger space. For additional crystals, additional address lines will be required. Thus, if a mosaic of 16x16 crystals is utilized, an additional 8 lines will be required, bringing the total number of lines for the preferred embodiment to (8+8)*4=64. These lines are grouped into four identical buses of 16 lines each. However, this reduction in lines may result in collisions at rather low event rates.

The count rate of the system can be improved substantially by further grouping of the crystals. For example, if the crystals are grouped in groups of four (2x2), and the crystals having the same position are grouped together, the system will require a total of [(6+8)*4]*4=224 lines.

Further count rate improvement can be obtained by increasing the size of the groups, thereby increasing the number of lines required.

It is thus seen that the present invention allows for a trade-off between the number of lines and the speed. In general, 32 lines is sufficient for most systems.

It should be understood, that were the electrodes connected directly to the computer, the number of lines required for a system having a mosaic of 16x16 crystals, each having 16x16 pixels would be 65536, a completely unwieldy number. Even the use of multiplexing and fast sampling would still require a very large number of lines.

The two most demanding applications for gamma camera are first pass and coincidence modes. In first pass a radio-isotope is injected into a vein leading to the heart. The first pass of the nearly undiluted radioactive material through the heart is measured -to assess the heart function. Since the measurement time is very short, high count rates must be achieved in order to collect meaningful statistics. Rates of 400,000 counts per second or more may be encountered during first pass. Since the projection of the heart is approximately 100 $cm^2$ the rate density is about 4,000 counts/$cm^2$-sec. On the assumption that half the events (on the average) split into two adjacent cells, the rate of threshold crossing is one and one half times the event rate or 600,000 counts per second (cps) for the system and 600 cps/$cm^2$.

On the individual cell level, where the size is very small, even assuming a band pass filter with a time-constant of 1 or several microseconds, there is no practical limitation on the system rate.

On the ASIC level, the ASIC resets its channels once the data is transmitted from one of its cells. If an event is detected in one cell after another cell has crossed the threshold, but before the other cell transmits its information and resets the ASIC, that information will be lost. This time is set by the one-shots of FIG. 10A at 420 nanoseconds, which leads to a nominal rate of $2.4 \times 10^5$ cps/ASIC. Since each ASIC serves 64 cells, the nominal density is $9.4 \times 10^4$ cps/cm$^2$, which poses no problem in achieving the required count rate.

On the system level, there are four buses, each is busy for 100 nanoseconds while data is transmitted. This leads to a maximum rate of $10^6$ cps/buss or a system rate of $4 \times 10^6$ cps versus the $6 \times 10^4$ cps required. This would result in an acceptable loss of counts. Alternatively, the busy time of the busses can be reduced by at least a factor of two by using faster A/D convertors.

Operation in a coincidence mode requires rates of up to $10^6$ per head. Since this is close to the limit for the preferred embodiment, for such systems a smaller grouping with a larger number of lines may be preferred.

The spatial response of a detector head comprised of a multitude of discrete detector cells is space variant. A small object placed above the cell center will produce an image significantly different from one placed at the boundary of two cells. A space invariant response can be achieved by moving the detector cells with a controlled motion parallel to the detector plane, such that the object is viewed, preferably with equal probability by all points in an area at least equal to the cell size. If this motion is monitored and compensated for, preferably on the fly, on an event by event basis, two performance improvements may result:

a) the detector performance will be spatially invariant with a resolution (separation power) of one cell.

b) the accuracy of location measurement will be equal to that of the accuracy of the determination of the motion of the head.

The dithering scan length should extend over at least one cell, preferably over an integer number of cells, for example one or two cells or more.

Data which is acquired at the varying positions of the head is reframed into an image pixels which correspond to fixed positions with respect to the patient. The size of the image pixels is smaller than, and generally much smaller than, that of the detector cells.

There is therefore provided, in accordance with a preferred embodiment of the invention, a gamma camera head comprising:

a plurality of signal sources, each associated with a pixel position, each said source producing a signal when a gamma ray absorption event occurs at or sufficiently close to its associated pixel, wherein said plurality of signal sources is associated with a contiguous extent of pixels; and a plurality of electronic circuits, each of which receives signals from at least two of the plurality of signal sources, wherein each said circuit receives said signals only from sources associated with non-contiguous pixels.

Preferably, at least two of the sources are connected by a common connection, preferably a permanent common connection to each of said plurality of sources.

There is further provided, in accordance with a preferred embodiment of the invention, a gamma camera head comprising:

a plurality of signal sources, preferably solid state sources, each associated with a pixel position, each of said sources producing a signal when a gamma ray absorption event occurs at or sufficiently close to its associated pixel;

an electronic circuit which receives non-multiplexed signals from all of said sources; and a plurality of signal lines connecting all of said sources to said circuit, wherein at least one of said lines connects more than one source to said circuit.

Preferably, the circuit comprises a plurality of circuits, each of which is connected by a common connection, preferably a permanent common connection, to at least two of said plurality of signal sources.

Preferably, signal source is connected to only one of said plurality of circuits.

In a preferred embodiment of the invention, each electronic circuit produces a signal related to an energy of the event whenever any of the signal sources from which it receives signals produces a signal greater than a predetermined threshold.

Preferably, said pixels are grouped into contiguous groups of contiguous pixels and wherein each of said plurality of circuits receives signals from only one pixel in each group.

Preferably none of said plurality of circuits receives said signals from contiguous pixels in two adjoining groups.

In a preferred embodiment of the invention, the number of said common connections is less than or equal to the number of contiguous pixels in a group. Preferably, the pixels are grouped in contiguous groups of contiguous pixels and wherein each of said plurality of circuits receives signals from only one pixel in each group.

There is further provided, in accordance with a preferred embodiment of the invention, a gamma camera head comprising:

a matrix of signal sources, preferably solid state signal sources, each associated with a pixel position and grouped into a plurality of geometrically similar groups, each group having a plurality of contiguous pixel elements; and a plurality of electronic circuits, each of which receives signals from one pixel element within each of a plurality of groups, each said pixel element having a similar geometric position within its respective group.

Preferably, each signal source produces a signal when a gamma ray absorption event occurs at or sufficiently close to its associated pixel position.

In a preferred embodiment of the invention, each electronic circuit also produces at least one signal indicating in which group of pixels the signal was generated.

Preferably, each electronic circuit also produces at least one signal indicating that; an event has occurred, the indicating signal preceding the energy signal in time.

In one preferred embodiment of the invention each group comprises four pixel elements. In other preferred embodiments of the invention each group comprises 2 or 9 pixel elements.

Preferably, the sources transmit said signals to said circuit independent of any interrogating signal to the sources.

Preferably, the sources are each associated with an array of contiguous areas on the camera, such that said signals represent events which occur at or near the associated area and wherein said circuit identifies events which generate signals in sources associated with two neighboring areas.

In a preferred embodiment of the invention the signal sources are associated with at least one normally insulating crystal in which free charge is produced when a gamma ray is absorbed therein. In a preferred embodiment of the invention the signal sources comprise a matrix of conductive elements on the crystal which collect the free charge.

In a preferred embodiment of the invention the at least one crystal comprises a mosaic of such crystals.

There is further provided, in accordance with a preferred embodiment of the invention, a gamma camera for imaging radiation emitted from or transmitted by an object, comprising:

a gamma camera head having a front, input, surface, and which produces signals when a photon associated with the radiation is detected by the head, indicative of the position of the detection on the input surface, at a given resolution; and a dithering system which differentially translates the detector head or the object in at least one direction parallel to the input surface by an amount at least equal to the given resolution but less than 50 times the given resolution during acquisition of the events.

There is further provided, in a preferred embodiment of the invention, a gamma camera for imaging radiation emitted from or transmitted by an object, comprising:

a gamma camera head having a front, input, surface, and which produces signals when a photon associated with the radiation is detected by the head, indicative of the position of the detection on the surface, at a given resolution; and a dithering system which differentially translates the gamma camera head or the object in two directions parallel to the front surface by an amount at least as large as the given resolution during acquisition of the signals.

Preferably the amount of differential translation is greater than twice or four times the given resolution.

In a preferred embodiment of the invention, the gamma camera includes circuitry which receives the signals and an indication of the position of the head and which distributes the events into an image matrix of pixels having a matrix resolution finer than the given resolution, said image matrix being referenced to the object.

Preferably, the event is distributed into an image pixel having a reference point closest to a reference point in the head, translated by the position indication.

In a preferred embodiment of the invention, events acquired at a plurality of head positions having a distance therebetween smaller than the given resolution are distributed to said image matrix.

In a preferred embodiment of the invention, the gamma camera includes an imaging system which provides an image of the distribution of the detected radiation based on the signals, the image having a second resolution which is substantially constant over the surface.

There is further provided, a gamma camera for imaging radiation emitted from or transmitted by an object, comprising:

a gamma camera head having a front, input, surface, and which produces signals when a photon associated with the radiation is detected by the head, indicative of the position of the event on the surface at a given resolution; and an imaging system which provides an image of the distribution of the detected radiation based on the signals, the image having a second resolution which is substantially constant over the surface.

Preferably the second resolution is substantially equal to the given resolution. The matrix resolution is preferably finer than the given resolution by any factor, for example by a factor of at least two or four.

In a preferred embodiment of the invention, radiation sources, whose captured radiation is spaced by a distance greater than the sum of the given resolution and the image pixel, will be separately imaged as sources which have a center spaced by the distance, substantially independent of the position of the capture of the radiation on the surface. Preferably, the image of a line source of constant width will have a constant width along its length for any inclination of the line on the surface. Preferably, the image of two point sources will have a substantially constant spacing independent of their position on the surface.

In a preferred embodiment of the invention, the gamma camera head comprises an array of detector elements, preferably solid state detectors, which produce said signals in response to the detection of the photons and wherein the spacing of the elements is substantially equal to the given resolution.

In a preferred embodiment of the invention the gamma camera head incorporates an array of solid state detector elements which produce said signals in response to the detection of the photons.

There is further provided, in accordance with a preferred embodiment of the invention, a gamma camera head for imaging gamma rays emitted from or transmitted by an object comprising:

a plurality of detectors, each having a physical extent and spacings which define a physical resolution of the head, each detector producing a signal when the head detects a gamma ray which is associated with a cell in an acquisition matrix having said physical resolution; and an image matrix into which said events are individually distributed, wherein said image matrix has a resolution which is finer than the physical resolution.

Preferably, the image matrix is referenced to the object and the distribution into the finer image matrix is determined by the amount of the translation.

Preferably, the events are subsequently redistributed into a second image matrix having a resolution different from the image matrix or physical resolution.

In one preferred embodiment of the invention, the second image matrix has a resolution which is poorer than the physical resolution by a non-integral value.

There is further provided, in accordance with a preferred embodiment of the invention, a gamma camera head for imaging gamma rays emitted by or produced in an object comprising:

a plurality of detectors, preferably, solid state detectors, each having a physical extent and having a spacing therebetween which define a physical resolution of the head, each detector producing a signal when the head captures a gamma ray which is associated with a pixel in an acquisition matrix having said physical resolution; and an image matrix into which said events are distributed, wherein said image matrix has a resolution which is poorer than the physical resolution by a nonintegral value.

There is further provided, in accordance with a preferred embodiment of the invention, a gamma camera comprising:

a gamma camera head as described above; and an imaging system which provides an image of the gamma rays based on the signals, having a resolution which is substantially constant over the surface of the head.

The invention will be more clearly understood from the following description of preferred embodiments thereof in conjunction with the drawings in which:

PREFERRED EMBODIMENTS OF THE INVENTION

Figure 1:
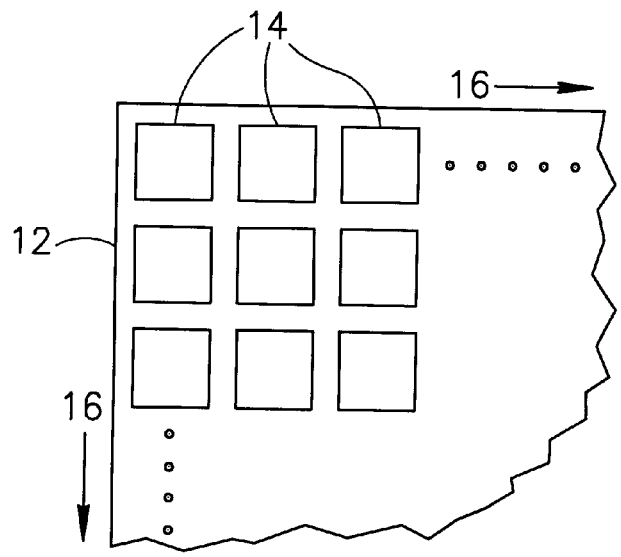
FIG. 1 is a schematic drawing of a bottom view of a crystal, in accordance with a preferred embodiment of the invention, having a matrix of 16×16 electrodes.
Figure 2:
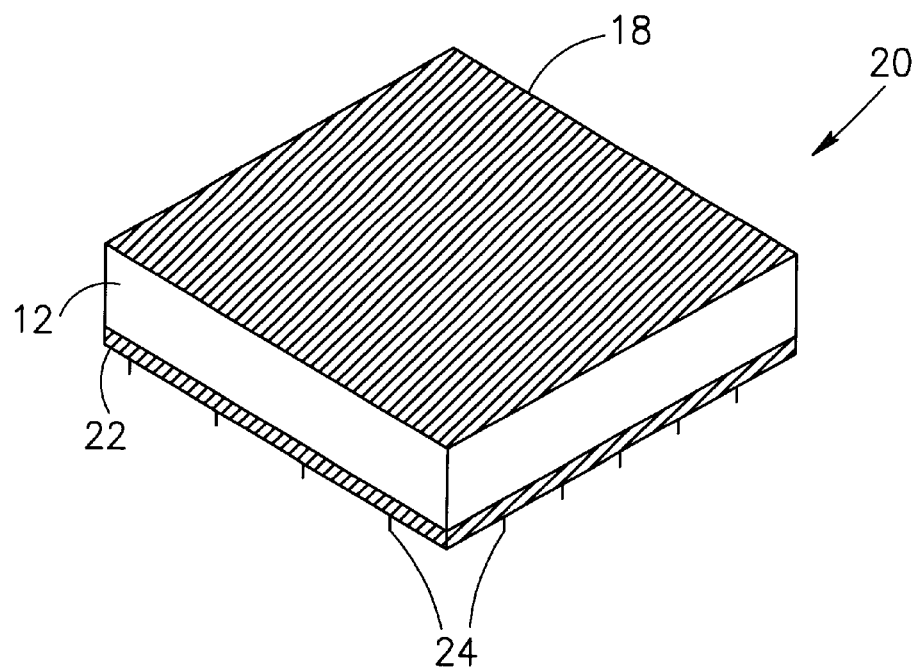
FIG. 2 is a schematic isometric drawing of a crystal module including ASICs, showing the top of the crystal of FIG. 1, in accordance with a preferred embodiment of the invention.
Figure 3A:
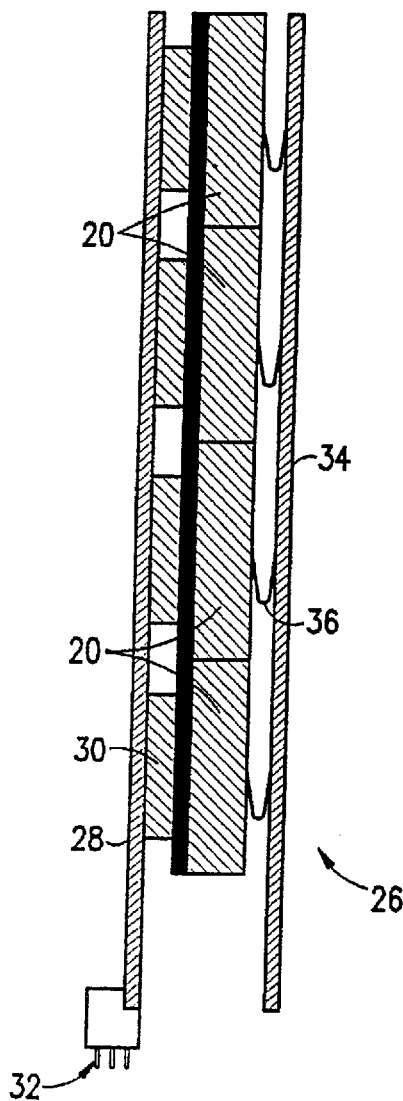
FIG. 3A is a schematic side view of a detector head including a plurality of crystal modules mounted on a mother board.
Figure 3B:
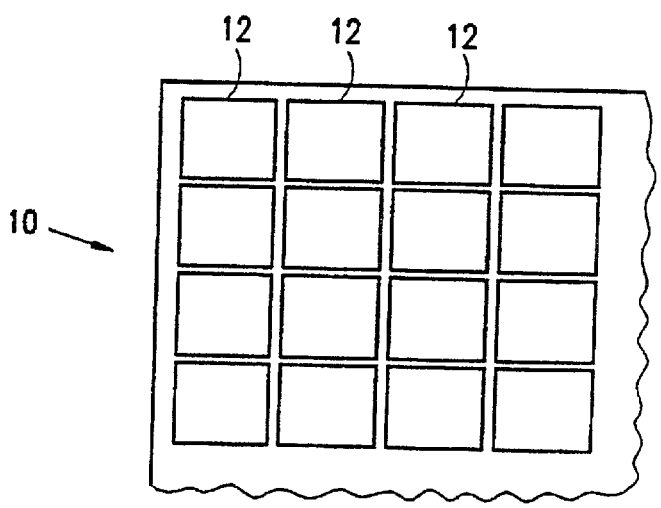
FIG. 3B is a schematic top view drawing of a portion of the detector head of FIG. 3A.

Reference is now made to FIGS. 1–3 which show the construction of a detector head 10 in accordance with a preferred embodiment of the invention.

In general, in preferred embodiments of the invention, a solid state gamma camera comprises detector head 10 which is made up of a mosaic of crystals 12 of CdTe (or alternatively of CdZeTe, $HgI_2$, InSb, Ge, GaAs, GaAlAs, PbS, PbSC or Si), each preferably associated with a module 20. One side of the crystal is preferably covered by a single, common, electrode 18 and the other side of the crystal is preferably covered by a rectangular (preferably square) matrix of closely spaced electrodes 14. This matrix of electrodes defines the cells or pixels of the gamma camera image. In a preferred embodiment of the invention, the matrix comprises 16×16 elements having a size of 2×2 mm. However, the size of the elements and the matrix size may vary over a relatively wide range depending on the desired spatial resolution and count rate.

Generally, a rectangular mosaic of crystals each with its associated matrix of elements is used to provide a camera of the required size. This mosaic may have a dimension of 16×16 crystals or greater.

FIG. 2 shows some details of one of modules 20, in accordance with a preferred embodiment of the invention. In particular FIG. 2 shows the common electrode 18, which faces outwardly from the module, a crystal carrier 22 which receives signals from electrodes 14 and which preferably includes processing electronics for processing these signals as described in detail infra. Connection pins 24 or other means for electrically connecting the modules to the rest of the gamma camera are also provided.

FIG. 3A shows one preferred method for connecting a plurality of modules 20 to form a detector head 26. A mother board 28 comprises a socket 30 for each module 20. socket 30 receives signals from pins 24 and transmits them to the rest of the system via a plug 32. A pressure plate 34 and associated thin pressure providing springs 36 are preferably provided to secure -the modules in place and to provide high voltage to the common electrode 18 associated with each module.

As indicated above, a common system would have 16×16 pixels on each of a 16×16 mosaic of crystal elements. This would lead to a matrix of 256×256 pixel elements. Addressing such a matrix using prior art methods would require a severe trade-off between the speed of the system (if the elements were serially addressed) and the complexity of the wiring if the pixels were addressed in parallel.

In accordance with a preferred embodiment of the invention, a method and apparatus for determining the position of events on the detector head is provided which combines high accuracy, high speed and reduced complexity.

Figure 4A:
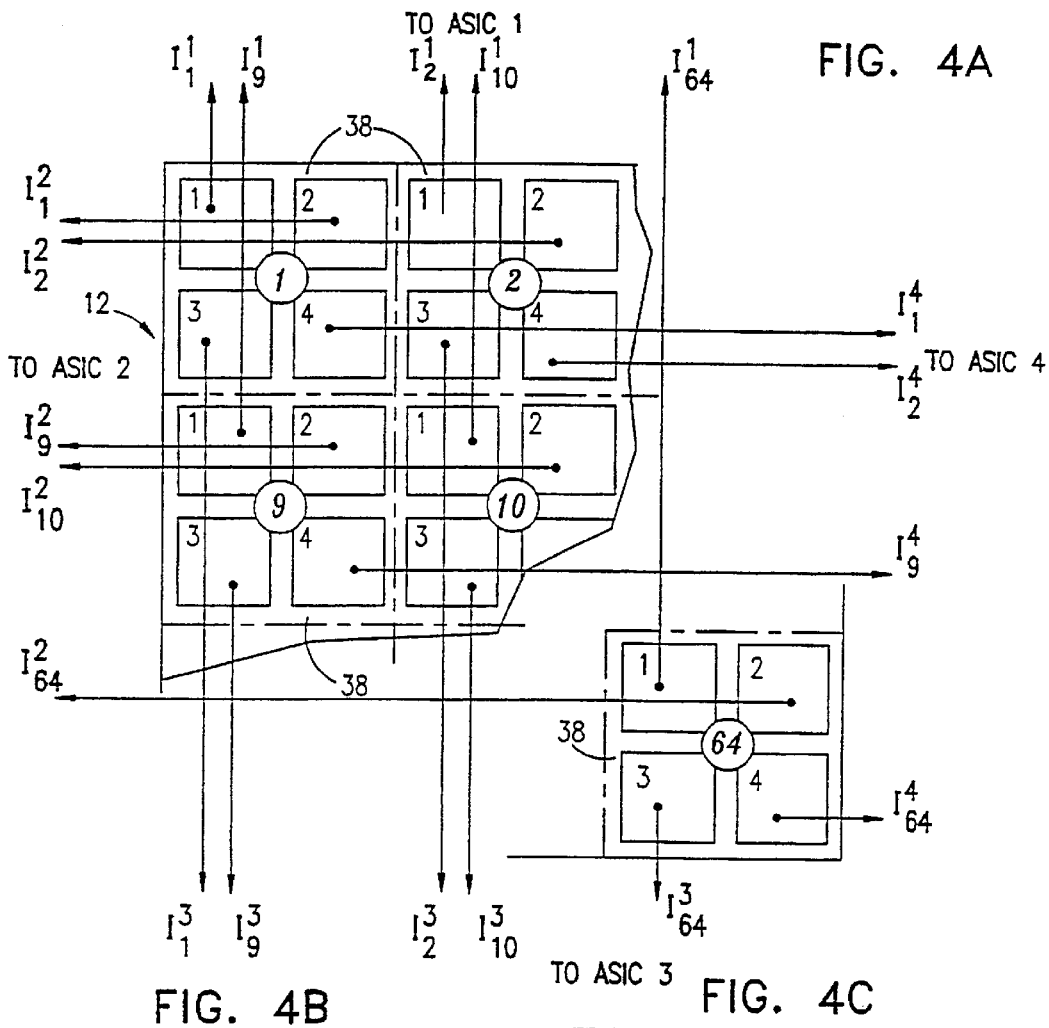
FIG. 4A shows a connection scheme for a portion of the electrodes on a crystal, in accordance with a preferred embodiment of the invention.

FIG. 4A shows connections to the electrodes on a crystal 12, in accordance with a preferred embodiment of the invention. In this embodiment, the pixels (=electrodes) are grouped in square 2×2 groupings 38 (delineated by dotted lines), with each pixel in a group being marked with one of the numbers 1–4 on FIG. 4. Similarly, each of the groups is designated by reference numbers 1–64, there being 8×8 groups of 2×2 elements.

Each electrical connection -to the elements is denoted, in FIG. 4A and in the subsequent figures by a reference $I_m^n$, where n designates the position of the element within its group and m is the number of the group. Each of the elements in the first position, namely the 64 elements numbered $I_m^1$ are connected to a first circuit called an ASIC 42 (shown in FIG. 5A), which is an acronym for Application Specific Integrated Circuit. Similarly, each of the elements in the other positions are separately connected to respective ASIC for those positions. Thus, in this preferred embodiment of the invention, the system includes four ASICs, one for each of the four positions in the group, with each ASIC having 64 inputs, one from each of the groups of elements. The four ASICs are preferably incorporated into crystal carrier 22, as indicated above.

Figure 4B:
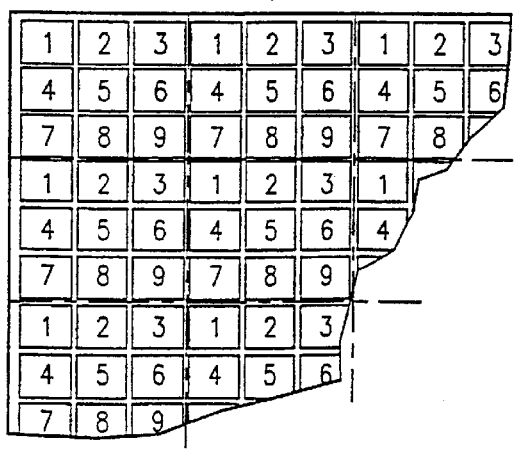
FIGS. 4B and 4C show alternative grouping schemes to that of FIG. 4A having a greater and lesser number of elements in each group.
Figure 4C:
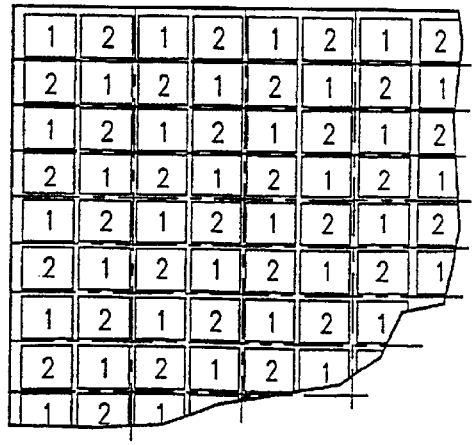

FIGS. 4B and 4C show two additional grouping schemes for the pixels. In FIG. 4B a 3×3 grouping is shown having 9 pixels per group. This system requires 9 ASICs and has a higher maximum rate than the system of FIG. 4A. FIG. 4B shows a system with only two pixels per group. This system while requiring fewer ASICs (only two) is proportionately slower than the systems of FIGS. 4A and 4B.

Figure 5A:
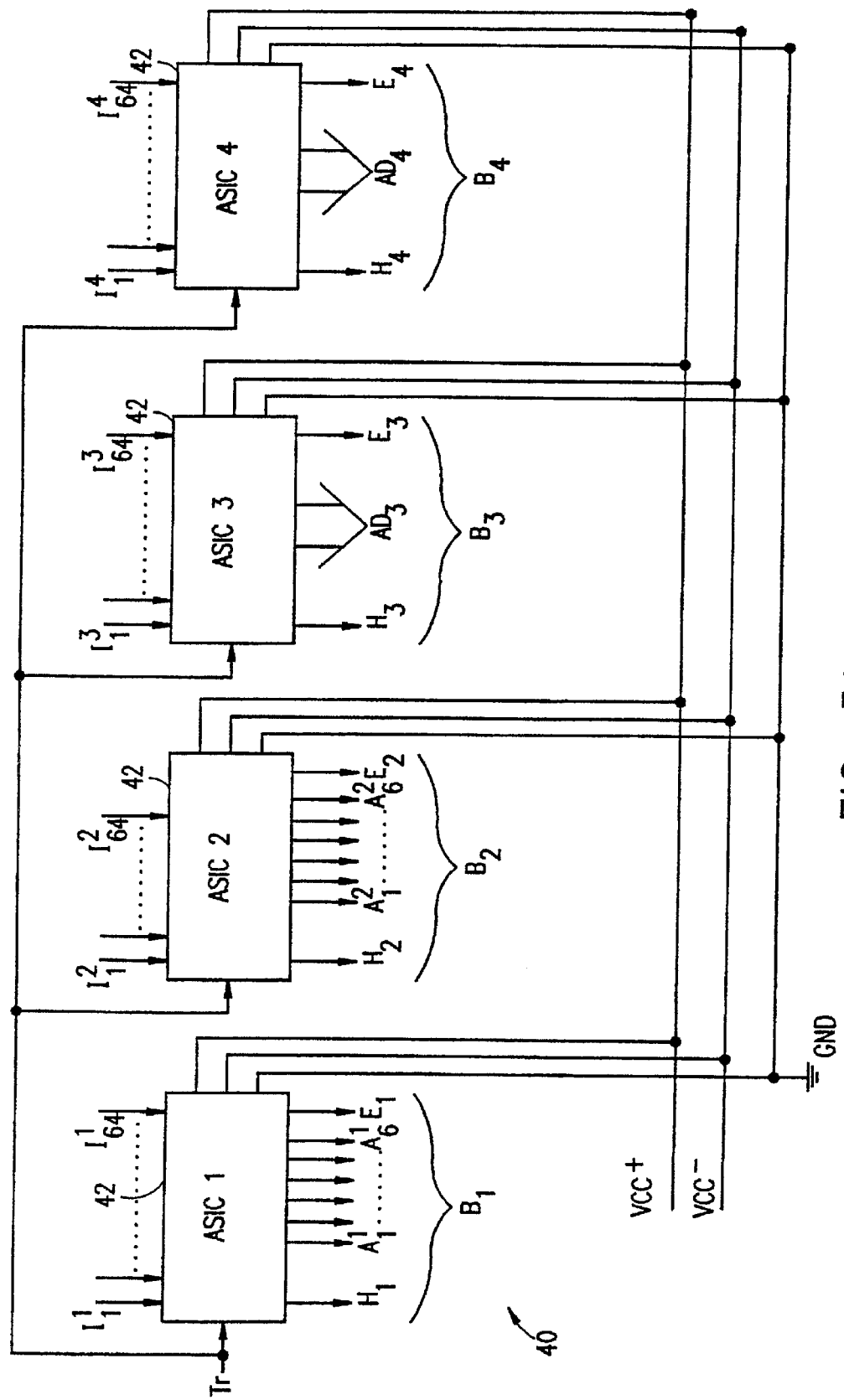
FIG. 5A is a block diagram of the circuitry on a module carrier for a single crystal, in accordance with a preferred embodiment of the invention.
Figure 5B:
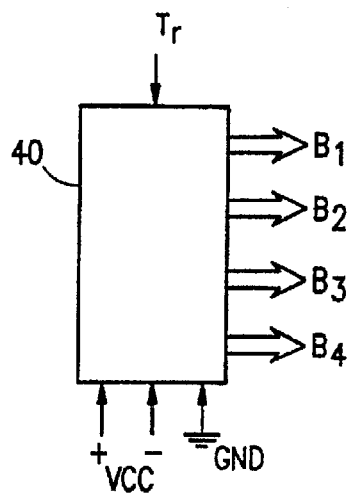
FIG. 5B is a more simplified block diagram of a single crystal module.

FIG. 5A and 5B are simplified and very simplified schematic, functional block diagrams of receiver circuitry 40 contained in carrier 22, i.e., for each module 20, in accordance with a preferred embodiment of the invention.

As indicated above, and as shown in FIG. 5A, each module comprises four ASICs 42 each having 64 data inputs. Each ASIC also receives a signal "$T_r$", whose function is described below and generates signals on eight lines $H_p$, $A_q^p$ and $E_p$ where p is the number of the ASIC and q is a number between 1 and 6. H is a signal which denotes if a signal associated with an event has been generated in any of the pixels associated with ASIC 42, the A lines identify the pixel associated with the ASIC in which the signal has been generated and E carries a, preferably analog, energy signal denoting the energy associated with the pixel. The group of 8 signal lines associated with the ASIC is denoted by $B_p$.

Figure 6A:
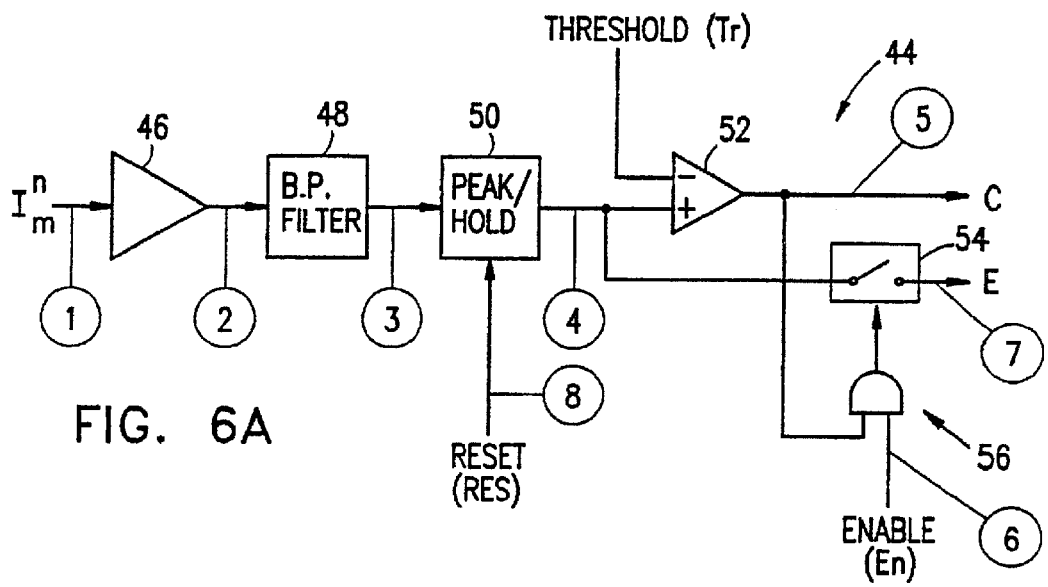
FIG. 6A is a simplified circuit diagram of an analog channel, in accordance with a preferred embodiment of the invention.

FIG. 6A shows some of the circuitry, indicated by reference number 44, associated with each pixel, contained in ASICs 42. The circuitry is thus repeated 64 times in each ASIC for the preferred embodiment described above.

A signal $I_m^n$ generated by an element is fed to an amplifier, preferably a charge to voltage amplifier 46. The amplified signal is preferably filtered using a band-pass filter 48, preferably an AC coupled low pass filter, which reduces the noise in the signal. A peak detector (and hold) circuit 50 is preferably used to detect and hold the peak value of the signal generated by amplifier 46. Circuit 50 is preferably reset periodically with a reset signal, RESET, which is generated elsewhere in the ASIC, as described below.

A comparator circuit 52, compares the detected peak signal with the threshold signal $T_r$ and generates an "event detected signal" "C" at position "5", if the detected signal is greater than the threshold value. In addition, the E signal, described earlier, is preferably the peak value of the detected signal. A switch 54 is enabled by an AND circuit 56 when the signal "3" is positive, i.e., when the peak detected value is higher than the threshold value.

Figure 6B:
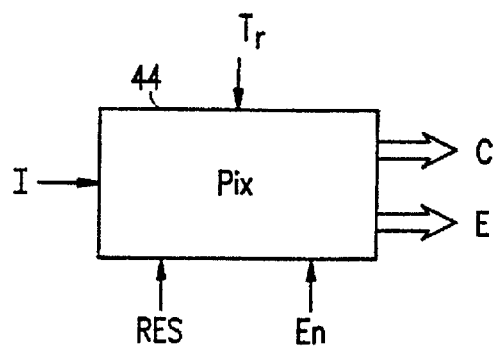
FIG. 6B is a simplified block representation of the circuit of FIG. 6A.

FIG. 6B shows a functional simplified version of circuitry 44, referring to circuit 44 as a "Pix" circuit.

Figure 6C:
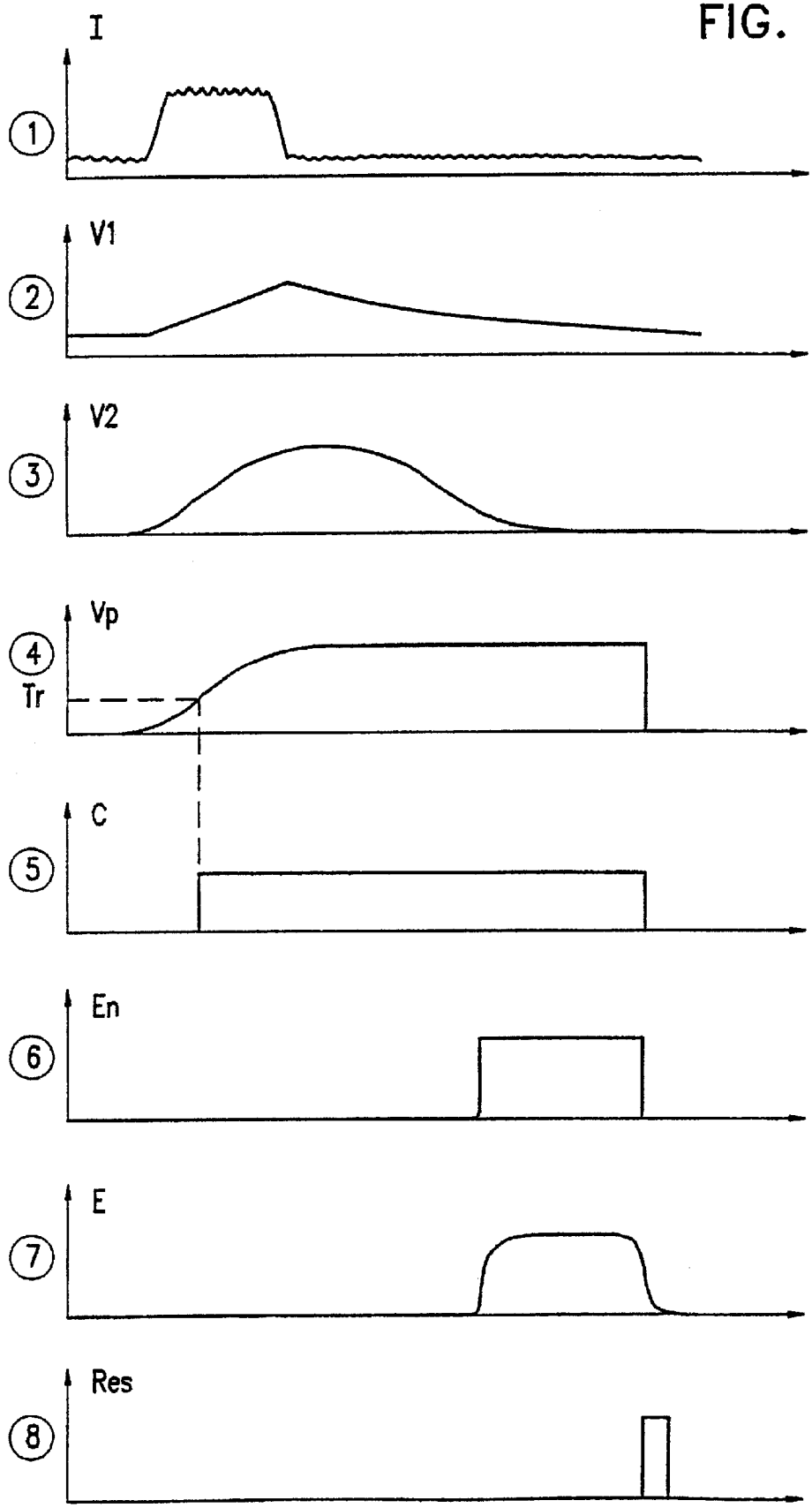
FIG. 6C shows the voltages and currents generated in the circuit of FIGS. 6A and 6B by an event.

FIG. 6C shows the timing and signals developed by the circuitry of FIGS. 6A and 6B, where each of the signal graphs is correlated with a particular test point in FIG. 6A. Signal "1" represents the current generated at a pixel by the occurrence of an event either within the pixel or, as described below, in a neighboring pixel. This current is, in effect, integrated in current-to-voltage amplifier 46 to produce signal "2" (charge). After filtering, the integrated signal becomes the more rounded signal "3" whose peak is less sensitive to the noise level of the original signal "2". The signal after the peak detector and hold circuit 50 follows the filtered signal until the filtered signal peaks and then holds that peak value. When the filtered circuit passes the threshold value, the event detected signal "C" is turned on as shown at "5." In response to the event detected signal shown in "5" and an enable signal shown in "6" is generated, and the energy signal "E" appears at the output "7". Finally, after detection of the event is complete, the reset signal, shown in "8" clears the peak/hold circuit enabling detection of the next event.

Figure 7A:
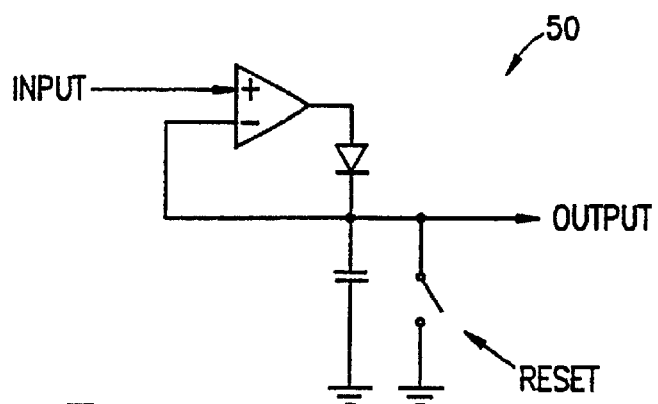
FIG. 7A shows a peak and hold circuit in accordance with a preferred embodiment of the invention.
Figure 7B:
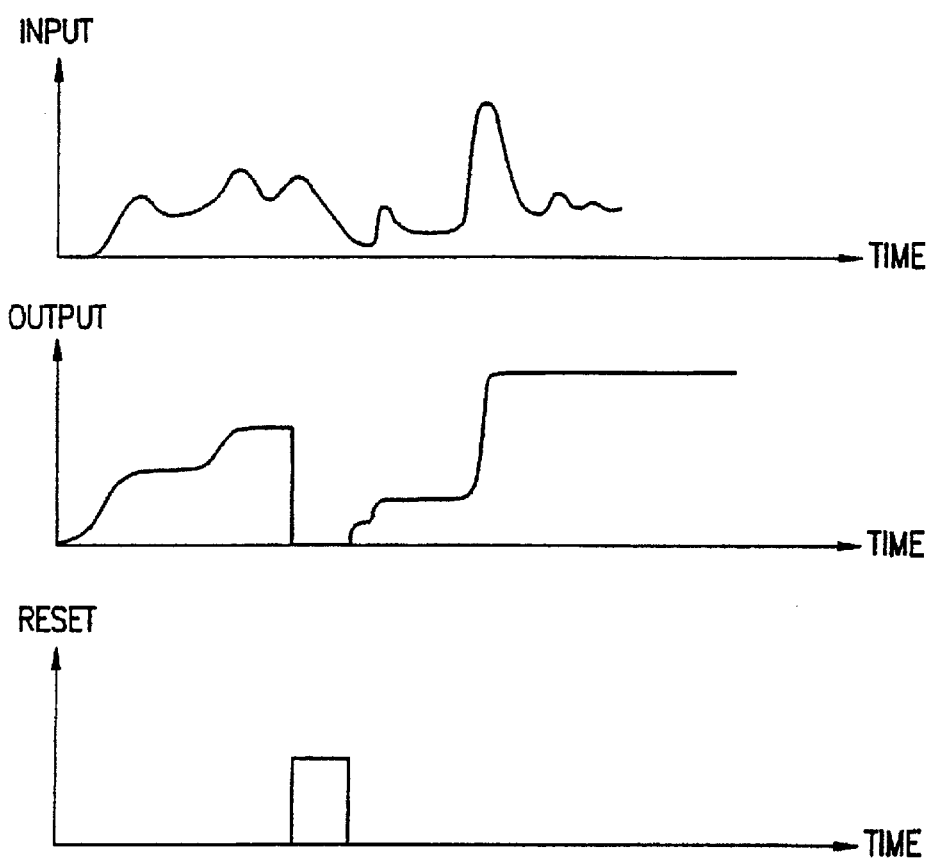
FIG. 7B shows the input and output voltages generated by the circuit of FIG. 7A for a particular current input.

FIG. 7A shows the details of peak and hold circuit 50 in accordance with one embodiment of the invention, with its response to an arbitrary signal (not one normally encountered in the present use of the circuit) shown in FIG. 7B. This circuitry is fairly common and any one of the many ways to perform this function may be used in place of the circuit of FIG. 7A. In the circuit shown in FIG. 7A, the signal at its output will be the historical peak value of its input for all times since the previous reset signal. When a reset signal is received, the output voltage is set at zero and, when the reset signal is removed, the output will again represent the historical peak value.

Figure 8:
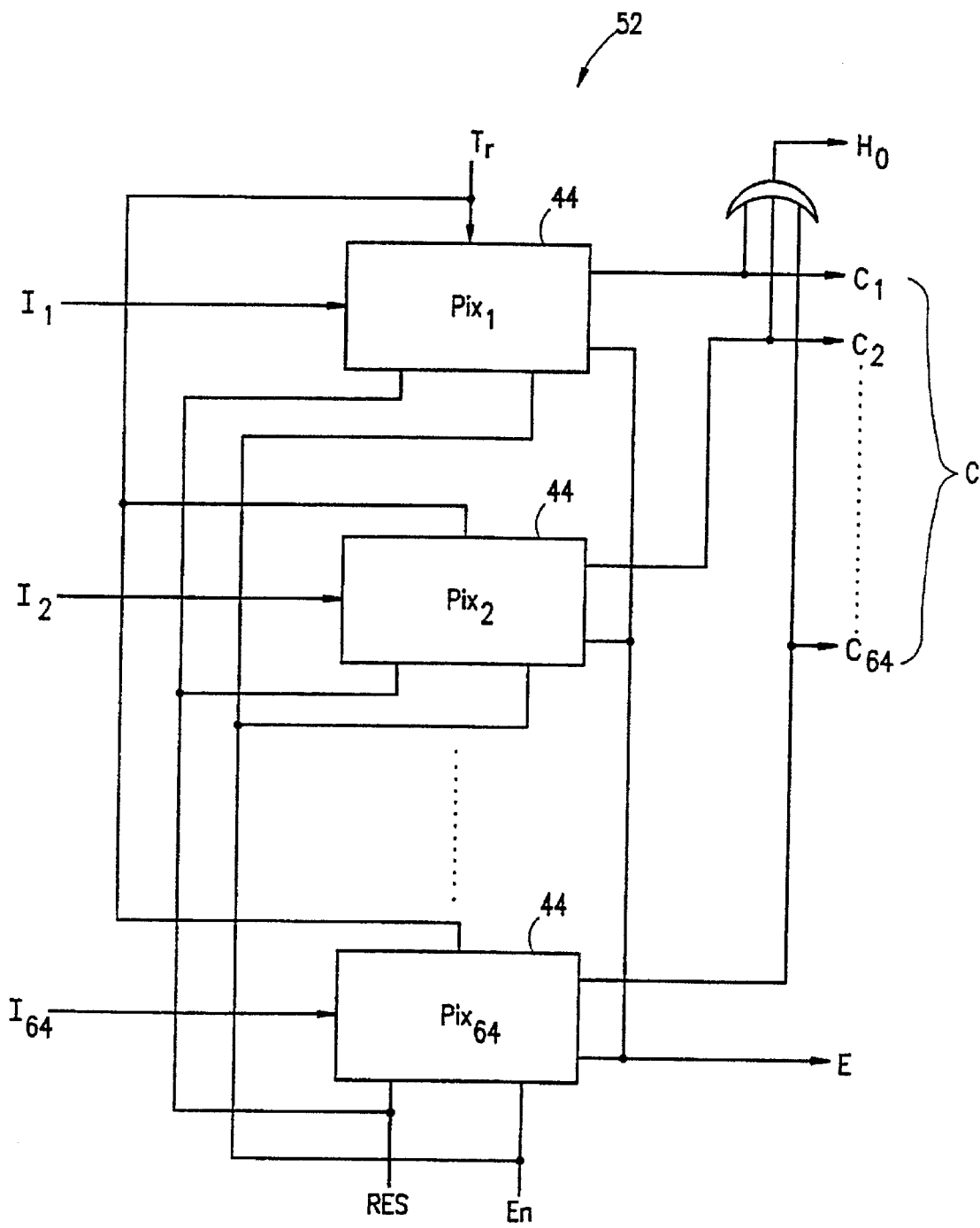
FIG. 8 shows a simplified block diagram of a front end portion of the ASIC, in accordance with a preferred embodiment of the invention.
Figure 9:
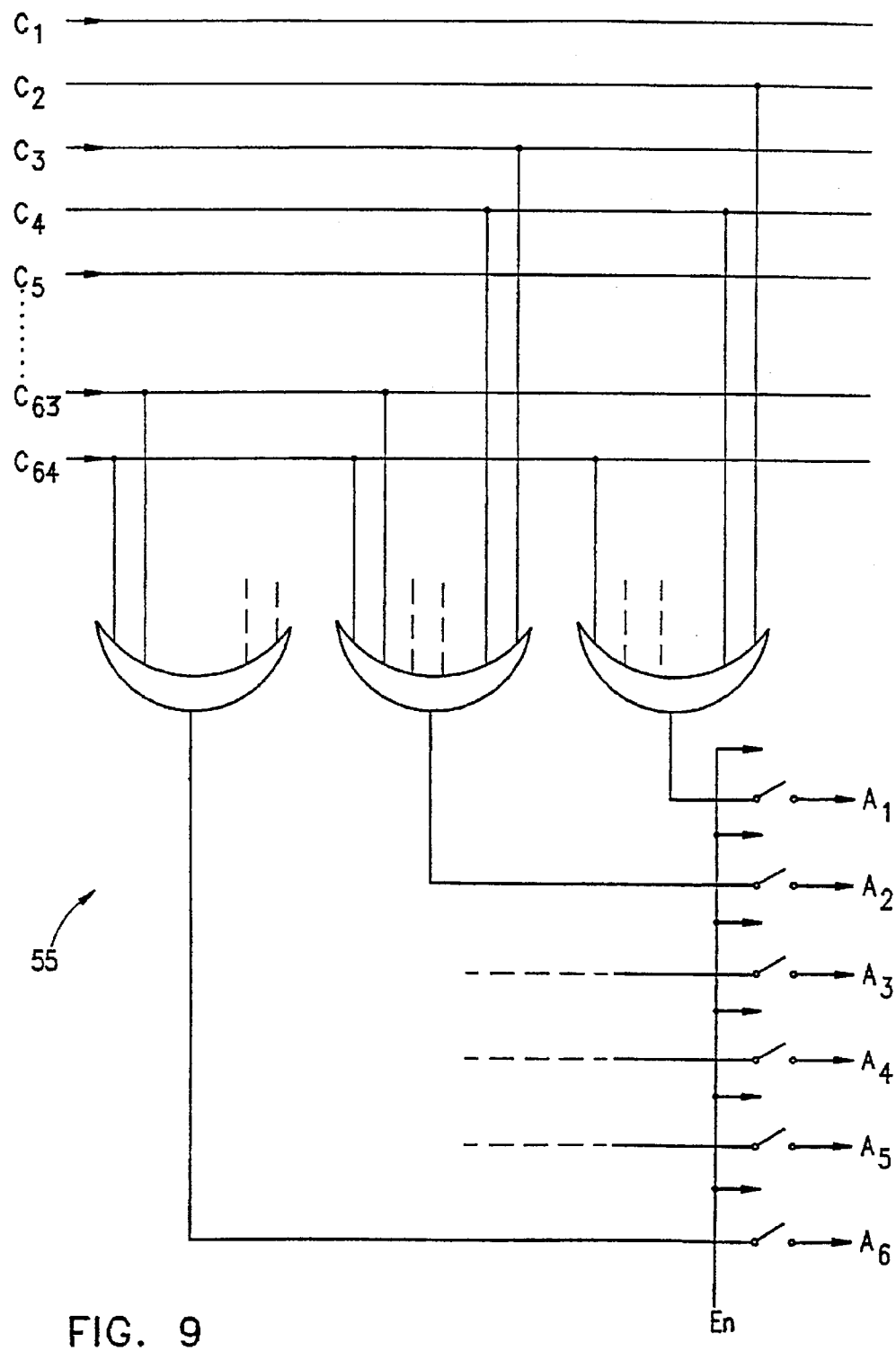
FIG. 9 is a 64 to 6 bit Address Encoder in accordance with a preferred embodiment of the invention.

FIGS. 8 and 9 show a preferred methodology by which the 64 Pix circuits 44 are interconnected to form front end circuitry 52. As indicated above, each of the Pix circuits 44 receives a single signal from one of the pixels associated with the particular ASIC. The E ("7") outputs are tied together to form a single E signal. This is based on the assumption that only a single event takes place in the crystal during any one cycle (between the minimum time between reset signals). For this assumption, only one of the E outputs of the Pix circuits will be enabled and the others will be zero. Thus the tying together of these signals does not cause any loss of information regarding the event.

Further, as shown in FIG. 8, the C signals are preferably combined in an "or" circuit to generate the previously mentioned reference H signal. The H signal thus denotes that one of the 64 pixels associated with the ASIC has generated a signal which may be associated with an event.

FIG. 9 shows preferred encoder circuitry 55 (also designated infra as ADRS circuitry) used to generate the signals $A_1$ to $A_6$, which as indicated above, identify which pixel (actually the group containing the pixel) is associated with the energy generated on the E line. This circuitry may, of course, be replaced by other circuitry, as known in the art, for generating the encoded address signals $A_1$ to $A_6$.

Figure 10A:
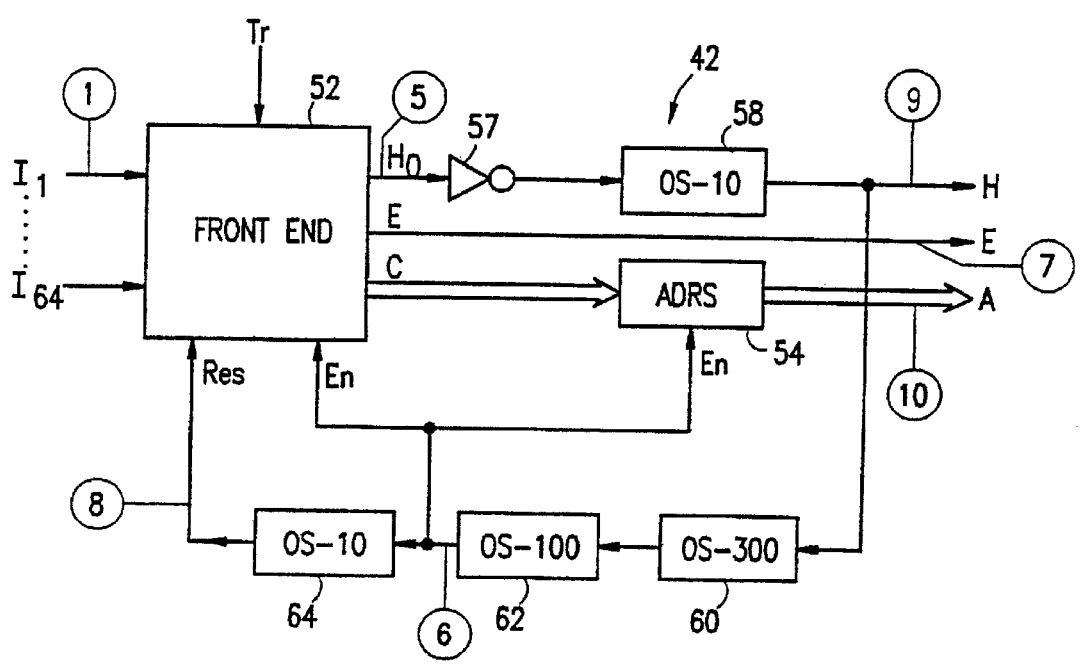
FIG. 10A shows the ASIC design logic in accordance with a preferred embodiment of the invention.
Figure 10B:
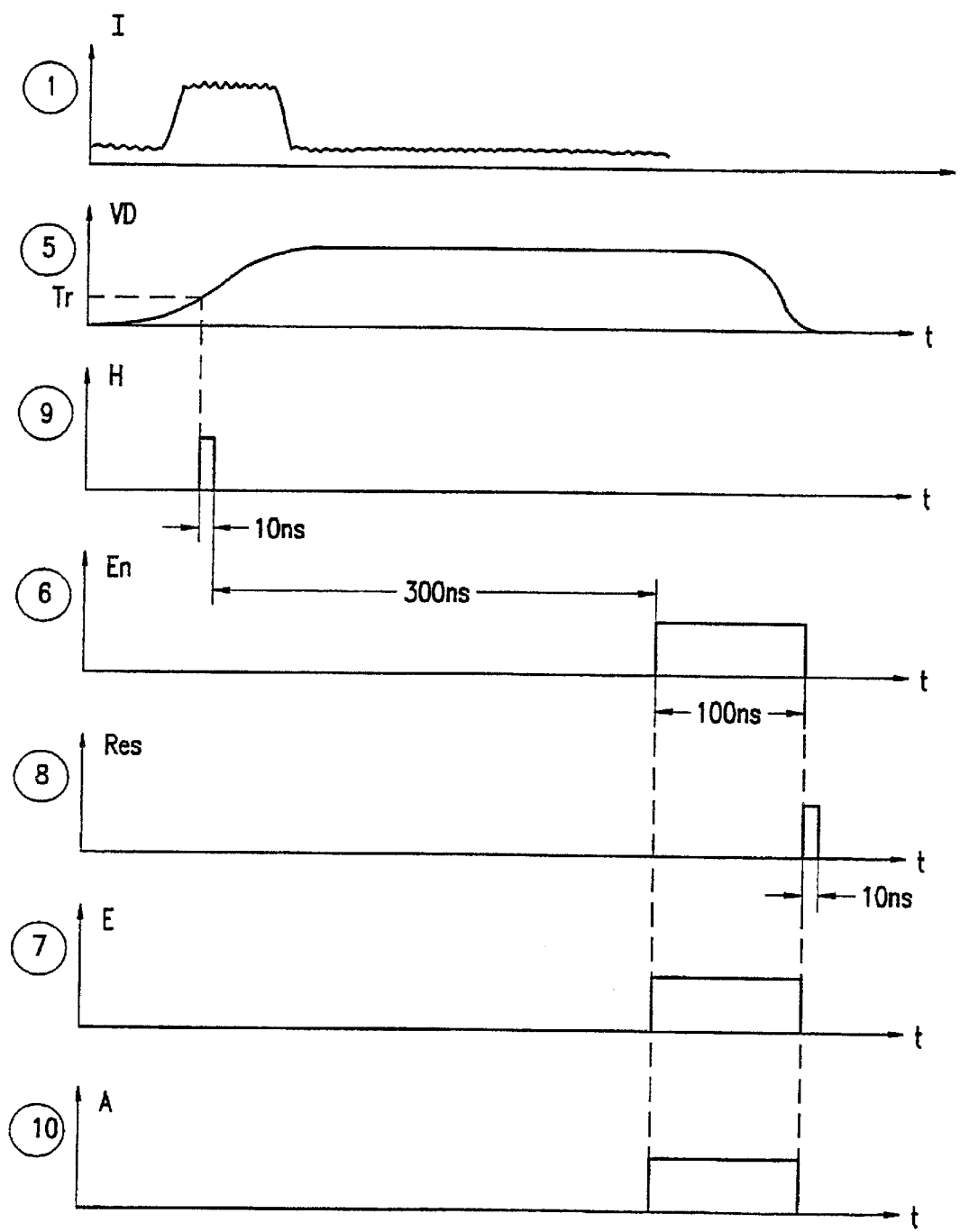
FIG. 10B is the timing associated with the circuit of FIG. 10A.

FIG. 10A shows a simplified block diagram of a complete ASIC 42 made up of the functional elements described above, together with additional circuitry. FIG. 10B shows the signals which are generated by ASIC, certain of which are repeated from FIG. 6C. As described above, front end 52 receives the 64 input signals associated with the ASIC and generates the H, E and C signals. The H signal feeds a "NOT" circuit 57 which changes the transitions of the H signal from positive to negative transitions and vice-versa. The "NOT"ed H signal is fed to a "one-shot" 58 which generates a 10 nanoseconds positive pulse when it detects a negative going transition. Thus, the combination of NOT circuit 57 and one-shot 58 produce a 10 nanosecond pulse (signal "H" at "9") almost immediately after the amplified signal "E" crosses the threshold value, $T_r$.

FIGS. 10A and 10B also show how the enable and reset signals are generated. The output of one-shot circuit 58 is fed to one shot circuits 60 and 62 which together operate to produce, at the output of one-shot 62, the $E_n$ pulse which is a 100 nanosecond pulse which starts 300 nanoseconds after the end of the pulse from one-shot 58. A one shot 64 produces a 10 nanosecond reset pulse following the end of the enable pulse. Also shown on FIG. 10B are preferred timing of the energy and position pulses described above.

Two characteristics should be noted for the above preferred embodiments. These characteristics are present for those embodiments of the invention in which it is desired to incorporate more fully events which take place near the border between two pixels or in which the transfer of energy from an incoming gamma ray takes place in two steps, as described above, in the summary of the invention.

It is observed that, in almost all cases, the transfer of energy (or more importantly, the generation of signals) takes place in adjacent pixels, or, more rarely, in pixels adjacent a corner. Thus, the method and apparatus described above utilizing the ASICs of the invention allows for the separate determination of the energy in each of the possible pixels associated with a given event and of the distribution of the energy among the pixels. This allows for accurate energy discrimination among events, for all events, including those events which generate signals in two or more pixels. The threshold value $T_r$ determines the minimum signal (energy) per pixel which is to be considered in the determination of the energy and position of an event. In a preferred embodiment of the invention, the threshold level is set at a low value, sufficient to block signals which arise from noise and leakage signals generated in the crystal. A threshold setting of several percent of the total energy for a pulse may be suitable in many situations. To the extent that noise and spurious signals generated in the crystal are small, the predetermined threshold could be zero or close to zero.

The position of an event whose signal is divided between two pixels will be determined based on the measured relative intensity of the signals and the source of the division. For example, for relatively low energies, where the major reason for energy division is the spreading of the charge cloud which is generated, the position is determined to be the pixel having the greatest signal value. For very high energies, where two step energy transfer is common, it may be desirable to place the event in the pixel having the smaller signal, when that signal is above a certain amplitude.

Figure 11A:
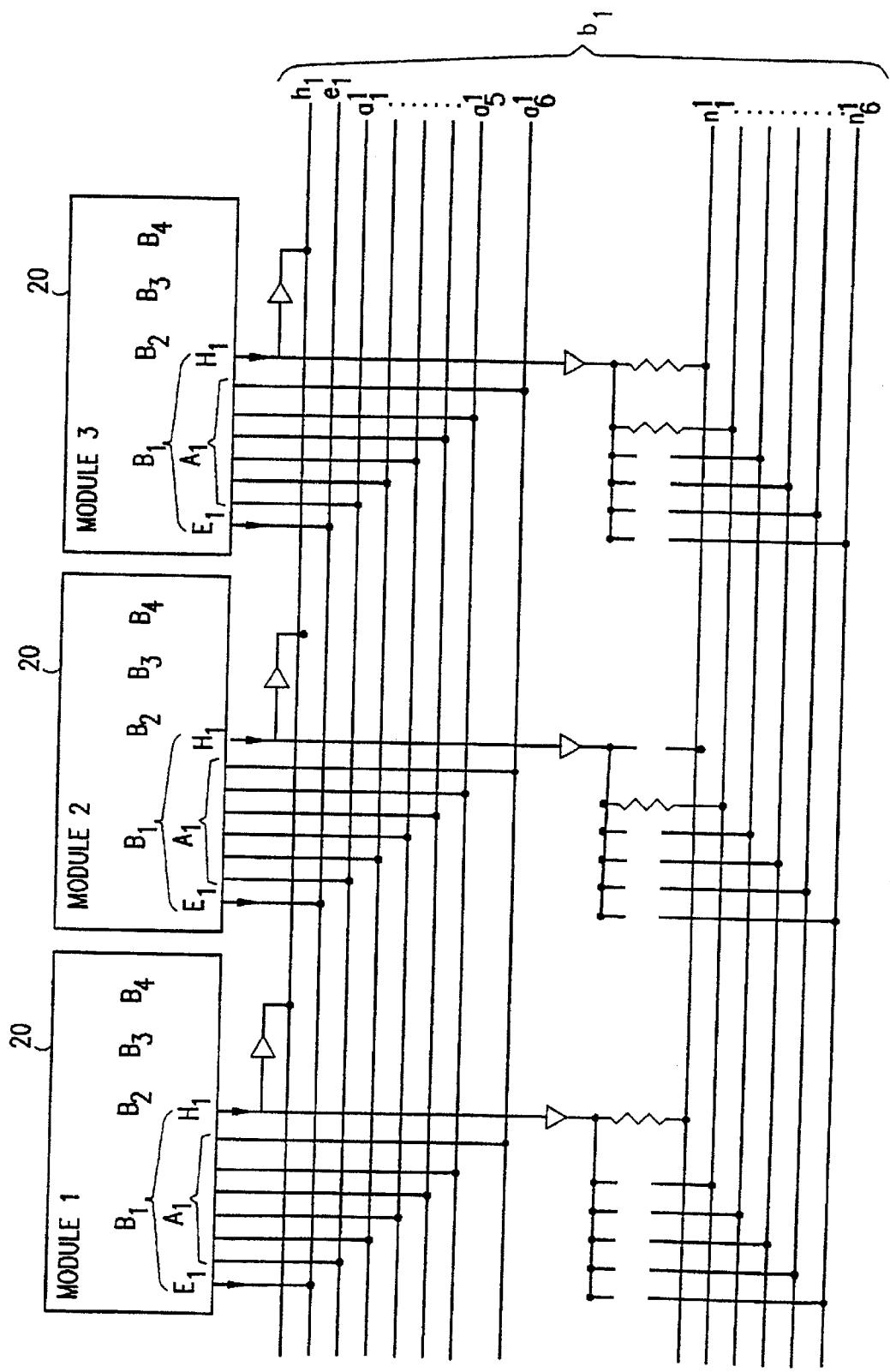
FIGS. 11A and 11B are simplified block diagrams showing the interconnection of modules on a motherboard in accordance with one preferred embodiment of the invention.
Figure 11B:
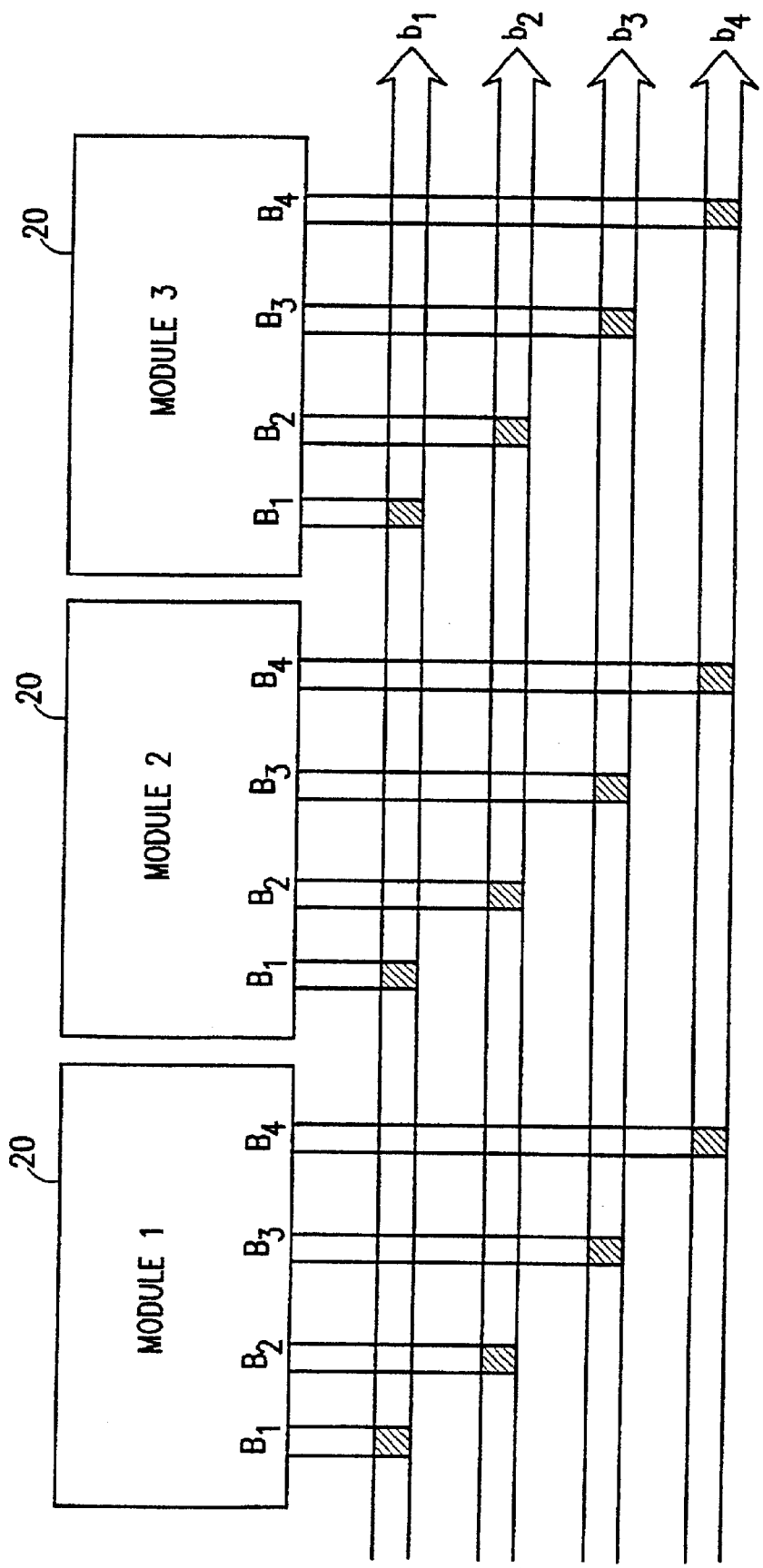

FIG. 11A shows how modules are interconnected, where only one event at a time over the face of the detector head is to be detected at any one time. In this case, the H line is utilized to generate an additional 6 bits of position information $n_1^1$ to $n_6^1$. FIG. 11B shows this operation in a more schematic form.

Figure 12:
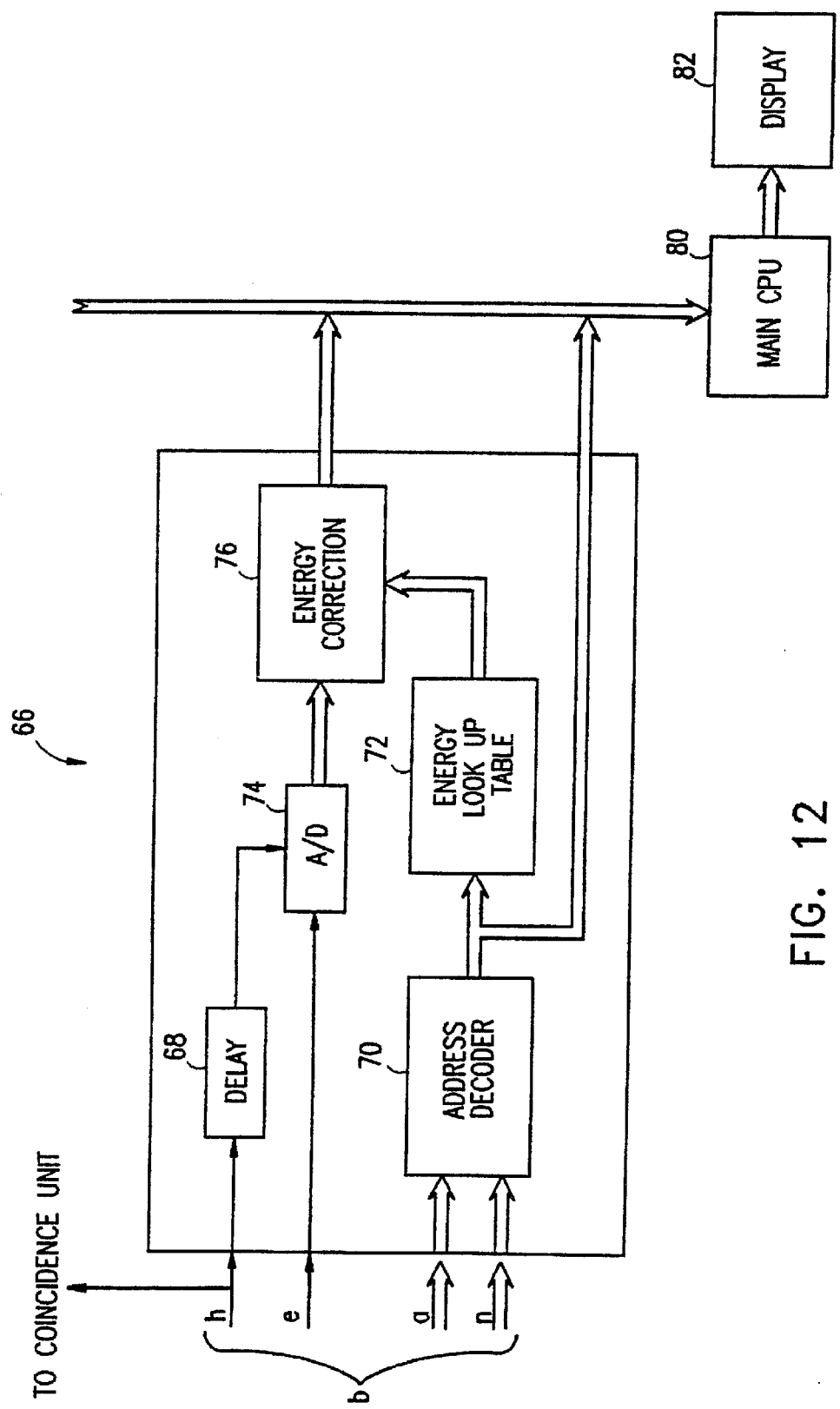
FIG. 12 is a representation of an acquisition unit in accordance with a preferred embodiment of the invention.

FIG. 12 is a partial schematic diagram of a "back end" acquisition unit 66 of a gamma camera utilizing a detector head as described above. Back end 66 receives the signals generated by ¼ of the pixels from the front end, namely the "event detected" pulse, which precedes the other pulses, the energy pulse and the encoded position signals, a and n.

The event detected pulse is delayed by delay circuitry 68 and the delayed pulse is used to trigger an A/D circuit 74. The position signals are decoded by an address decoder 70 and this address is used to look up a correction factor in look-up table 72. This correction is used, in energy correction circuitry 76, to correct the (possibly) partial energy generated in pixels which feed the acquisition unit or due to pixel to pixel variations. This energy, together with the position of the pixel on which it was detected, are fed to CPU 80.

The above discussion has been limited to the case where a single event happens during a measurement interval, such as that shown in FIG. 10B. In the event that more than one event occurs during a measurement interval, the signals generated must be ignored. In addition, if the energy is detected in more than one adjacent pixel, these energies must be added and the sum of the energy used to determine if an event is within a determined energy range, which indicates a valid event.

Figure 13:
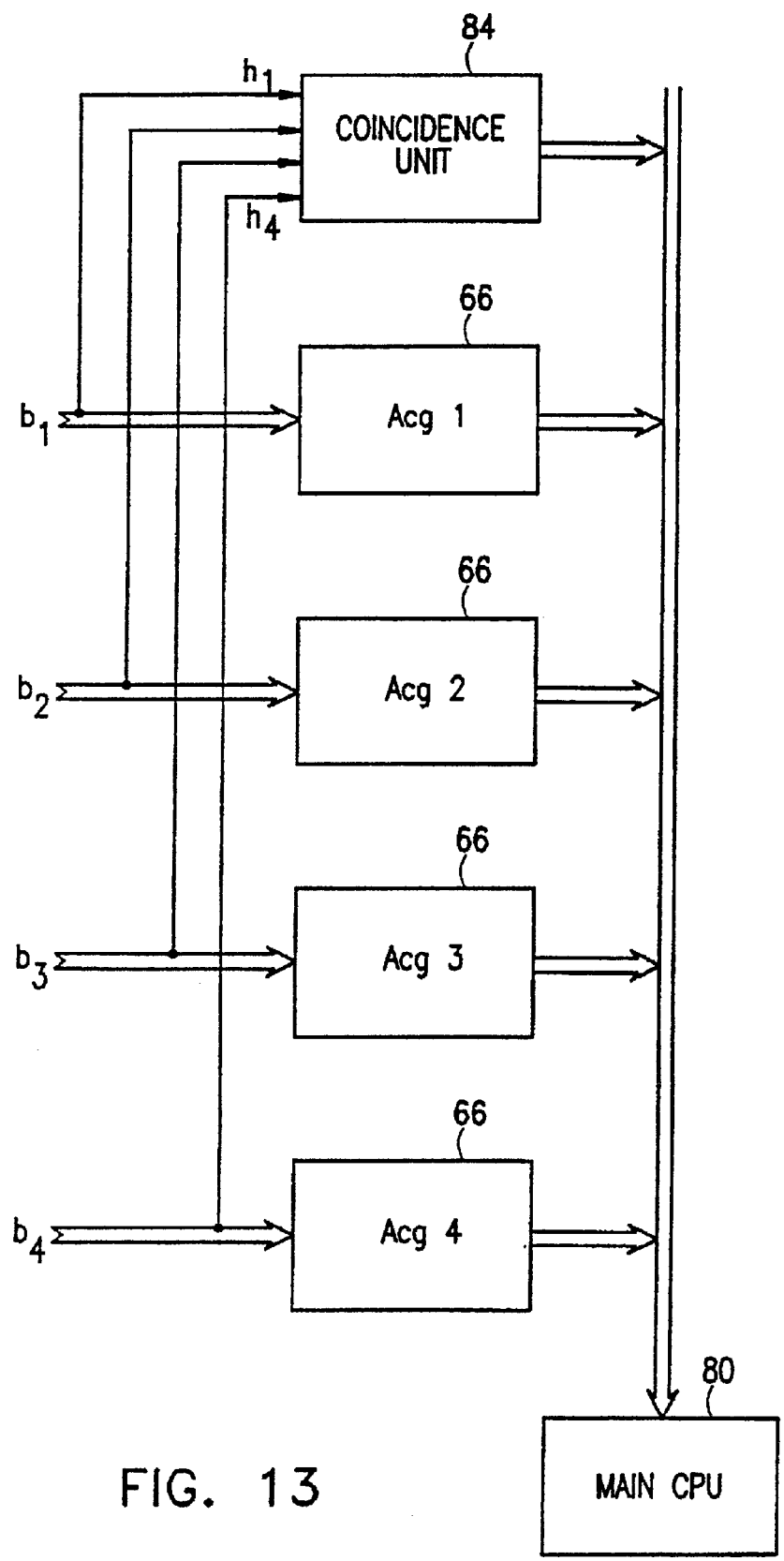
FIG. 13 is a block diagram of an acquisition board in accordance with a preferred embodiment of the invention.

These functions may be carried out in CPU 80 and in a coincidence unit 84 shown in FIG. 13, which is a schematic block diagram showing connection between the four acquisition units 66 which make up the preferred embodiment of the invention. Coincidence unit 84 receives the event detected signals from all four acquisition units. If multiple, closely spaced, signals are detected by the same acquisition unit 66, coincidence unit 84 instructs main CPU 80 to ignore the event. If closely spaced and/coincident signals are detected by different acquisition units, the CPU is informed that it must take into consideration the possibility that the signals may be from a single event (if they are from adjacent pixels) or are the result of separate events (if they are from non-adjacent pixels). If the signals are from non-adjacent pixels, the energy signals are treated as separate events. If they are from adjacent pixels the energy signals are summed and form the basis for determination of the acceptability of the event. This acceptability is determined by comparing the summed energy (or the energy from a single pixel, where only one pixel produces a signal) to a range of energies to determine if the event was probably produced by a primary gamma ray. Such "windowing" is well known in the art.

In CPU 80, sensitivity correction, namely, a correction for the spatially varying probability of detection of events (caused by variations in either the intrinsic sensitivity of the crystal or of the intrinsic transmission of an overlying collimator) is performed. Many methods of correction, such as partial event summation, event skipping, event adding, etc. are known, and can be used with the present invention.

Finally, for events which cause signals to be generated in adjacent pixels, the true position of the event must be determined. If the gamma ray energy is low, the event should normally be assigned to the pixel with the highest signal. If the energy is high, the event can be divided between the various pixels, preferably based on a computed probability that the event occurred in each of the various pixels; or, the event can be placed in the pixel with the lower signal, so long as that signal is greater than some given value.

It should be appreciated that many variations are possible on the above described systems, within the scope of the invention. In particular, as mentioned in the summary of the invention, various divisions of the pixels into ASICs may be used. For example, more than 4 ASICs, for example 9 ASICs for a 3×3 grouping of pixels, may be used.

It is also possible to use fewer ASICs, utilizing a single ASIC for more than one crystal, with each ASIC having a greater number of input lines. In the extreme case only 4 ASICs, each receiving signals from one-fourth of the pixels (or 2 ASICs for the 2×1 system shown in FIG. 4C) is possible, in principle.

Furthermore, the unit shown in FIG. 13 which, as described, receives signals from the entire head, may be used to receive signals from only a portion of the pixels. This allows for multiple simultaneous events to be acquired, so long as they do not occur in ASICs served by the same acquisition unit. In this regard, it appears to be desirable for each acquisition unit to be associated with non-adjacent ASICs. This allows for more optimal distribution of hotspots among the acquisition units.

In addition, while the invention is described with respect to a detector head having a mosaic of a large number of particular types of crystals, this description is based on a practical situation of crystal availability, electronics reliability and manufacturing and service considerations. However, the addressing methods which have been described are equally applicable to any type of matrix for the detection of gamma events utilizing a single crystal or even one crystal per pixel. It is also applicable to types of detectors other than crystals. In the case of a single crystal or one crystal per pixel, it would be possible to utilize a hexagonal matrix of the pixels and only 3 ASICs.

Furthermore, the present invention is also applicable to a gamma camera head utilizing a scintillator crystal wherein the matrix of electrodes is replaced by a plurality of photo-receptors which generate a signal in response to light produced in the crystal by an event. Other sources of signals related to gamma ray absorption events may also be detected in accordance with the present invention.

Figure 14:
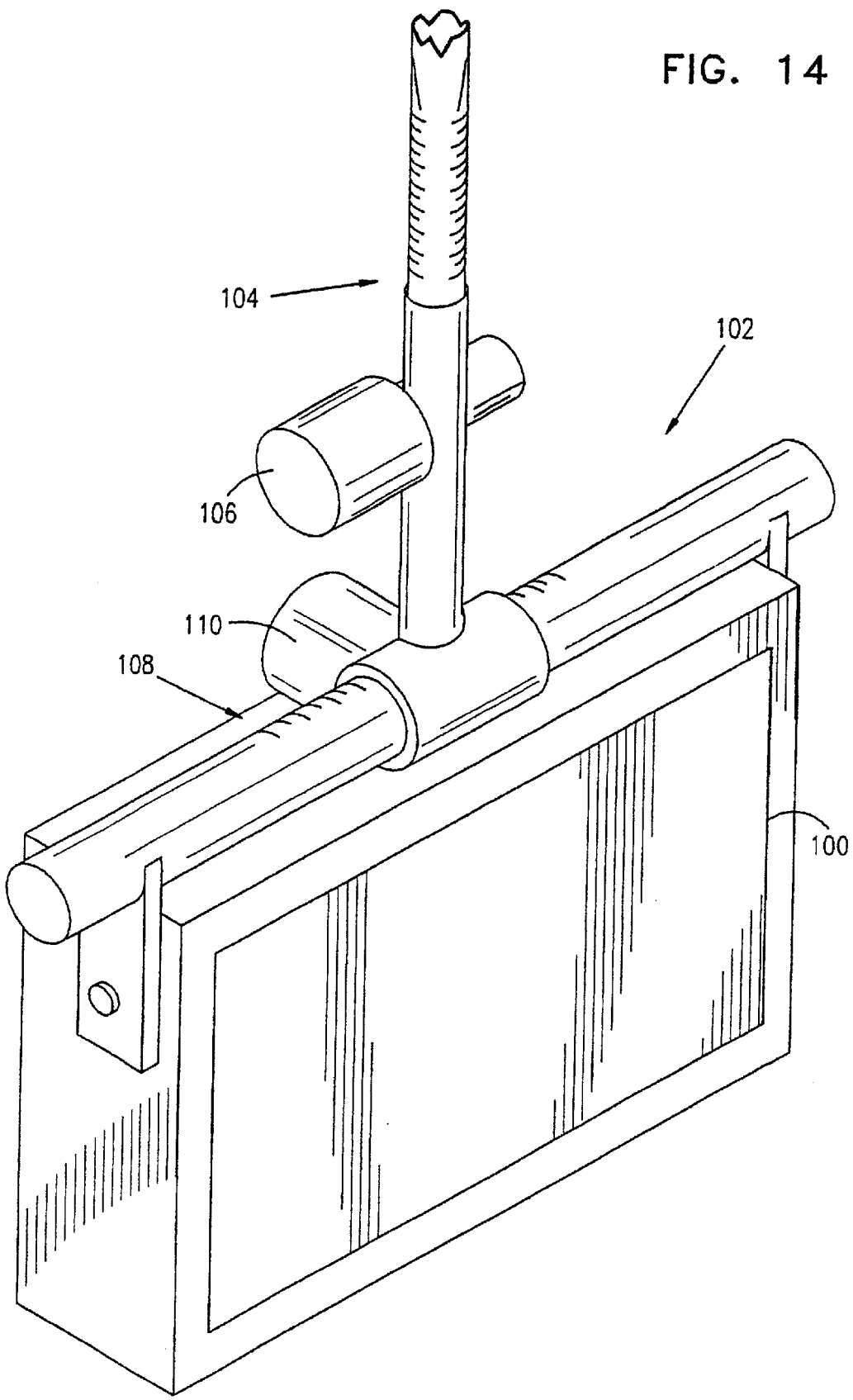
FIG. 14 shows, schematically, a system for providing a uniform resolution for solid state gamma cameras.

FIG. 14 shows, very schematically, a head 100 of a solid state gamma camera mounted on a dithering fixture 102. Dithering fixture 102 comprises a vertical dithering arrangement 104, including a motor 106, which is operative, in a preferred embodiment of the invention, to dither the position of the head in a first direction, parallel to the front surface of the head. Dithering fixture 102 also comprises a horizontal dithering arrangement 108, including a motor 110, which is operative to dither the position of the head in a second direction parallel to the surface of the head and perpendicular to the first direction. While translation of the gamma camera head is most desirable translation of the source of the gamma rays is also possible.

Alternatively, a single motor may be used to perform the dithering and a gear box may be used to provide dithering in two directions.

The spatial response of a detector head comprised of a multitude of discrete detector cells is space variant. A small object placed above the cell center will produce an image significantly different from one placed at the boundary of two cells. A space invariant response can be achieved by moving the detector cells with a controlled motion parallel to the detector plane, such that the object is viewed, preferably with equal probability by all points in an area at least equal to the cell size. If this motion is monitored and compensated for, preferably on the fly, on an event by event basis, two performance improvements may result:

a) the detector performance will be spatially invariant with a resolution (separation power) of one cell.

b) the accuracy of location measurement will be equal to that of the accuracy of the determination of the motion of the head.

The dithering scan length should extend over at least one cell, preferably over an integer number of cells, for example one or two cells or more.

In operation, the dithering system changes the position of the head in both directions such that during any acquisition the position is moved over a distance of at least one cell. However, the system is distinguished from full body scanning systems in which the position of the head is changed by a large amount, generally an amount larger than the extent of the field of view of the camera and always more than about 50 detector cell units. Since the acquisition time for any view is relatively long and the distance to be traversed is relatively small, such position dithering is relatively easy to perform. Preferably, the dithering steps are only a fraction of a cell or the dithering motion is continuous.

Data which is acquired at the varying positions of the head is reframed into image pixels which correspond to fixed positions with respect to the patient. The size of the image pixels is smaller and, generally much smaller, than that of the detector cells.

In a first embodiment of the invention, data is acquired continuously while the camera head is moved. In this embodiment of the invention, if the size of the image pixel is 1/n times the size of the detector cell, the dithering is n times as fast in one direction as the other.

In a second embodiment of the invention, the camera head moves in steps, each of which is 1/n of the physical resolution element. In this embodiment of the invention, the head moves by the increment in one direction and then, while stationary in that direction it moves in a transverse direction either in steps of 1/n or continuously such that the time spent at each of the n transverse positions is the same.

It should be noted that, for SPECT imaging, dithering may only be required in the longitudinal direction.

During acquisition, the system computer (not shown in FIG. 14), which receives both the detected event information and information as to the dithering displacement, reframes the data which is received into the above-mentioned image pixels which correspond to fixed positions with respect to the patient. In an especially preferred embodiment of the invention, these image pixels are substantially smaller (preferably by a factor of 2 or more, and more preferably by a factor of 4–16) than the actual detector cell size, which is generally limited by the size of the solid state detectors themselves. This division need not be an integral, i.e., the detector and image pixel boundaries need not coincide.

By using such a dithering/rebinning system in accordance with the invention, one of the outstanding problems of solid state cameras, namely the non-uniform resolution of the camera is overcome.

In particular, where the camera head utilizes an array of detectors, the detectors have a physical size and spacing (referred to herein as a "detector cell") which define the ultimate resolution of the system and the accuracy with which the position of an event can be measured. When an event is acquired in a given detector cell, the event is ascribed to a fixed point within that cell, preferably, the center of the cell. The event is then reframed into the image pixel having its center closest to the center of the cell. While, in the preferred embodiment of the invention, the position of image pixels and detector cells are generally defined by their centers, other definitions can be used in the practice of the invention.

In a further preferred embodiment of the invention, synthetic image matrix elements are created by adding a random number, preferably equal to or smaller than the dithering step, to the actual position of the image pixel. In this way, a matrix having a plurality of pixels for each dithering element is created. This method is useful for providing images of varying resolution based on the acquired data.

In particular, absent the addition of the random number, any rebinning of the data to achieve a resolution which is not an integral multiple of the dithering step would result in artifacts. If, for example, the dithering step were 1.5 mm and an image having a resolution of 4 mm were desired, rebinning of the data would result in non-uniform resolution and sensitivity over the image.

One additional advantage of dithering in accordance with this aspect of the invention is thus seen to be that it allows for the generation of images having an integrally or non-integrally better or poorer resolution than the physical resolution, while preserving the uniform resolution and sensitivity characteristic of the invention.

As is well known in the art, the point or line source response of a solid state camera depends on the position of the source with respect to the detector cell boundaries. A diagonal line source, for example, will generally be imaged as a "staircase" or a line having varying width due to this varying resolution. When the dithering/reframing system of the present invention is utilized, the resolution of the system is constant over the entire face of the camera and is substantially equal to the detector cell size.

Furthermore, while the system resolution is limited to the size of the detector cell, and sources which are less than one cell apart cannot be resolved, a system in accordance with the invention is generally capable of reliably distinguishing two counts which are spaced by a fraction more than a single cell, so long as the fraction is greater than the image pixel size. Moreover, while such distances, when they are resolved in a prior art system, are resolved in integral detector element spacings (such that two sources spaced 1.5 cells apart may be imaged as being in adjoining cells or spaced apart by a full cell), in an image acquired according to the present invention, point and line sources will be spaced by their true spacing (to within the image pixel size). Thus, two point sources which are 1.5 pixels apart will be imaged as two sources having a width of 1 cell and a spacing between them of 0.5 cells, such that their centers are 1.5 cells apart. Of course such a system does require that the electronics of the system and the display be capable of handling and displaying the higher image pixel resolution.

It should be clearly understood that, while in a preferred embodiment of the invention, the dithering/reframing system described may be used in conjunction with a solid state gamma camera such as that described above with respect to FIGS. 1–13, dithering and reframing is effective in producing the advantages of uniform consistent resolution when used with any solid state camera as is known in the art or with any camera in which the pixels are delineated by a detector cell. For example, the dithering/reframing system is equally applicable to systems having a single scintillator crystal for each detector and for systems in which a single crystal is used for a plurality of sensors of the type described above or of any other type. In particular, the invention as described with respect to FIG. 14 is not meant to be limited by the invention described with respect to FIGS. 1–13. However, the system is especially suited to non-anger gamma cameras in which the physical spacing of detection elements defines the resolution of the system.

The present invention has been described in detail with respect to preferred embodiments thereof, however, this description is not limiting as to the scope of the invention which is defined by the following claims:

1. A gamma camera head comprising:
   a plurality of signal sources, each associated with a pixel position, each said source producing a signal when a gamma ray absorption event occurs at or sufficiently close to its associated pixel, wherein said plurality of signal sources is associated with a contiguous extent of pixels; and
   a plurality of electronic circuits, each of which receives signals from at least two of the plurality of signal sources, wherein each said circuit receives said signals only from sources associated with non-contiguous pixels.

2. A gamma camera head according to claim 1, wherein each signal source is connected to only one of said plurality of circuits (42).

3. A gamma camera head according to claim 1, wherein each electronic circuit produces a signal related to an energy of the event whenever any of the signal sources from which it receives signals produces a signal greater than a predetermined threshold.

4. A gamma camera head according to claim 1, wherein said pixels are grouped into contiguous groups of contiguous pixels and wherein each of said plurality of circuits receives signals from only one pixel in each group.

5. A gamma camera head according to claim 4 wherein none of said plurality of circuits receives said signals from contiguous pixels in two adjoining groups.

6. A gamma camera head according to claim 4 wherein each electronic circuit also produces at least one group indication signal indicating in which group of pixels the source produced signal was generated.

7. A gamma camera head according to claim 4 wherein each electronic circuit also produces at least one signal (H) indicating that an event has occurred, the event indicating signal preceding an energy signal produced by it in time.

8. A gamma camera head according to claim 4, wherein each group comprises four pixel elements.

9. A gamma camera head according to claim 4, wherein each group comprises nine pixel elements.

10. A gamma camera head according to claim 4, wherein each pixel group comprises two pixel elements.

11. A gamma camera head according to claim 4, wherein said sources transmit said signals to said circuit independent of any interrogating signal to the sources.

12. A gamma camera head according to claim 4 wherein said sources are each associated with an array of contiguous areas on the camera, such that said source produced signals represent events which occur at or near the associated area and wherein said plurality of circuits identifies events which generate signals in sources associated with two neighboring areas.

13. A gamma camera according to claim 4, wherein the signal sources are solid state signal sources.

14. A gamma camera head according claim 4, wherein the signal sources are associated with at least one normally insulating crystal (20) in which free charge is produced when a gamma ray is absorbed therein.

15. A gamma camera head according to claim 4 wherein, each electronic circuit that receives a source produced signal produces an indication of the group from which it received the source produced signal.

16. A gamma camera head according to claim 15 and including additional circuitry that receives group indications from said plurality of circuits and determines the location of an event that produced the source produced signals, responsive to the group indications.

17. A gamma camera head according to claim 16 wherein the additional circuitry determines the location of an event responsive to an identification the circuit or circuits of the plurality of circuits that received said source produced signals.

18. A gamma camera head according to claim 4, wherein said sources transmit said signals to said circuit independent of any interrogating signal to the sources.

19. A gamma camera head in accordance with claim 1, wherein said sources transmit said signals to said plurality of circuit independent of any interrogating signal to the sources.

20. A gamma camera head according to claim 1 wherein said sources are each associated with an array of contiguous areas (12) on the camera, such that said source produced signals represent events which occur at or near the associated area and wherein said plurality of circuit identifies events which generate signals in sources associated with two neighboring areas.

21. A gamma camera head according to claim 1 wherein the signal sources are solid state signal sources.

22. A gamma camera head according to claim 1 wherein the signal sources are associated with at least one normally insulating crystal (20) in which free charge is produced when a gamma ray is absorbed therein.

23. A gamma camera head according to claim 22 wherein the signal sources comprise a matrix of conductive elements (14) on the crystal which collect the free charge.

24. A gamma camera head according to claim 22 wherein the at least one crystal comprises a mosaic of such crystals.

25. A gamma camera head comprising:
   a matrix of signal sources, each associated with a pixel position and grouped into a plurality of geometrically similar groups, each group having a plurality of contiguous pixel elements; and a plurality of electronic circuits, each of which receives signals from one pixel element within each of a plurality of groups, each said pixel element having a similar geometric position within its respective group.

26. A gamma camera head according to claim 25 wherein each signal source produces a signal when a gamma ray absorption event occurs at or sufficiently close to its associated pixel position.

27. A gamma camera head according to claim 25 wherein each electronic circuit also produces at least one group indication signal indicating in which group of, pixels the source produced signal was generated.

28. A gamma camera head according to claim 27 and including additional circuitry that receives group indications from said plurality of circuits and determines the location of an event that produced the source produced signals, responsive to the group indications.

29. A gamma camera head according to claim 28 wherein the additional circuitry determines the location of an event responsive to an identification the circuit or circuits of the plurality of circuits that received said source produced signals.

30. A gamma camera head according to claim 25 wherein each electronic circuit also produces at least one signal (H) indicating that an event has occurred, the event indicating signal preceding an energy signal produce by it in time.

31. A gamma camera head according to claim 25, wherein each group comprises four pixel elements.

32. A gamma camera head according to claim 25 wherein each group comprises nine pixel elements.

33. A gamma camera head according to claim 25, wherein each pixel group comprises two pixel elements.

34. A gamma camera head according to claim 25, wherein said sources transmit said signals to said plurality of circuits independent of any interrogating signal to the sources.

35. A gamma camera head according to claim 25, wherein said sources are each associated with an array of contiguous areas on the camera, such that said source produced signals represent events which occur at or near the associated area and wherein said plurality of circuits identifies events which generate signals in sources associated with two neighboring areas.

36. A gamma camera according to claim 25, wherein the signal sources are solid state signal sources.

37. A gamma camera head according to claim 25 wherein the signal sources are associated with at least one normally insulating crystal (20) in which free charge is produced when a gamma ray is absorbed therein.

* * * * *